(12) United States Patent
Kim et al.

(10) Patent No.: US 11,013,435 B2
(45) Date of Patent: May 25, 2021

(54) ELECTRONIC DEVICE AND METHOD FOR MEASURING BIOMETRIC INFORMATION

(71) Applicant: Samsung Electronics Co., Ltd., Gyeonggi-do (KR)

(72) Inventors: Jihwan Kim, Suwon-si (KR); Sehoon Kim, Seoul (KR); Jungmo Kim, Yongin-si (KR); Jooman Han, Seongnam-si (KR); Choonghee Ahn, Hwaseong-si (KR); Jeongyup Han, Suwon-si (KR); Taeho Kim, Cheongju-si (KR); Jeongmin Park, Hwaseong-si (KR); Seungeun Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 85 days.

(21) Appl. No.: 15/937,668

(22) Filed: Mar. 27, 2018

(65) Prior Publication Data
US 2018/0276448 A1      Sep. 27, 2018

(30) Foreign Application Priority Data

Mar. 27, 2017   (KR) .......................... 10-2017-0038756

(51) Int. Cl.
*A61B 5/1455* (2006.01)
*G06K 9/00* (2006.01)
(Continued)

(52) U.S. Cl.
CPC .......... *A61B 5/14551* (2013.01); *A61B 5/684* (2013.01); *A61B 5/6898* (2013.01);
(Continued)

(58) Field of Classification Search
CPC .. G06K 9/00067; G06K 9/0002; A61B 5/684; A61B 5/743; A61B 5/7246;
(Continued)

(56) References Cited

U.S. PATENT DOCUMENTS

2009/0287070 A1   11/2009   Baker, Jr.
2011/0245622 A1   10/2011   McKenna
(Continued)

OTHER PUBLICATIONS

European Patent Office, European Search Report for Application No. EP 18162823.1, dated Aug. 14, 2018, 8 pages.

*Primary Examiner* — Amandeep Saini

(57) ABSTRACT

An electronic device and method for measuring biometric information are provided. The electronic device includes at least one light emitter; light receiver; and a processor. The processor is configured to emit light outside of the electronic device through the at least one light emitter, obtain, through the light receiver, light reflected by an external object among the emitted light, obtain a signal generated based on at least a portion of the reflected light and corresponding to the external object, output guide information related to a location of the external object when the signal satisfies a first designated condition, and obtain biometric information about the external object when the signal satisfies a second designated condition. When a finger of a user finger of the electronic device is not accurately located at a bio sensor, by guiding an accurate grip location, biometric information about the user can be accurately measured.

15 Claims, 25 Drawing Sheets

(51) Int. Cl.
*G06F 3/0488* (2013.01)
*G06F 3/16* (2006.01)
*A61B 5/00* (2006.01)
*G06F 3/044* (2006.01)

(52) U.S. Cl.
CPC .......... *A61B 5/7221* (2013.01); *A61B 5/7246* (2013.01); *A61B 5/743* (2013.01); *G06F 3/0488* (2013.01); *G06F 3/167* (2013.01); *G06K 9/0002* (2013.01); *G06K 9/00067* (2013.01); *G06F 3/044* (2013.01)

(58) Field of Classification Search
CPC . A61B 5/7221; A61B 5/6898; A61B 5/14551; G06F 3/167; G06F 3/044; G06F 3/0488
USPC .......................................................... 382/125
See application file for complete search history.

(56) References Cited

U.S. PATENT DOCUMENTS

| | | | |
|---|---|---|---|
| 2011/0245691 | A1 | 10/2011 | Silber |
| 2013/0289372 | A1* | 10/2013 | Imran ................. A61B 5/1459 600/339 |
| 2014/0275808 | A1* | 9/2014 | Poeze .................... A61B 5/742 600/300 |
| 2015/0208962 | A1* | 7/2015 | Baker, Jr. ............ A61B 5/1495 600/331 |
| 2015/0359436 | A1 | 12/2015 | Shim et al. |
| 2016/0317088 | A1* | 11/2016 | Fougere ............... A61B 5/0002 |
| 2017/0337413 | A1* | 11/2017 | Bhat .................... G06K 9/0012 |
| 2018/0246595 | A1* | 8/2018 | Chae ..................... G06F 3/0416 |

* cited by examiner

ELECTRONIC DEVICE AND METHOD FOR MEASURING BIOMETRIC INFORMATION

CROSS-REFERENCE TO RELATED APPLICATION(S)

This application is related to and claims priority to Korean Patent Application No. 10-2017-0038756 filed on Mar. 27, 2017, the entire disclosure of which is hereby incorporated by reference.

TECHNICAL FIELD

Various exemplary embodiments of the present disclosure relate to an electronic device and method that can accurately measure biometric information about a user of an electronic device.

BACKGROUND

While use of portable electronic devices such as a smart phone or a wearable device increases, various functions are provided to the electronic device.

The electronic device may provide a health care service that can check a user's health management.

For example, the electronic device may measure the user's biometric information through a photoplethysmography (PPG) sensor and calculate a heart rate.

In order to obtain biometric information, when a user finger of the electronic device contacts a PPG sensor, the electronic device does not guide whether the user finger is accurately located at the PPG sensor.

SUMMARY

To address the above-discussed deficiencies, it is a primary object to provide an electronic device and a method thereof that can accurately measure biometric information about a user of the electronic device by guiding an accurate grip location of a bio sensor, when the user of the electronic device does not accurately locate a finger at the bio sensor (e.g., PPG sensor).

The present disclosure has been made in view of the above problems and further provides a computer readable recording medium in which a program is recorded that performs a method of measuring biometric information using an electronic device.

In accordance with an aspect of the present disclosure, an electronic device includes at least one light emitter; a light receiver; and a processor, wherein the processor is configured to emit light to the outside of the electronic device through the at least one light emitter, to obtain light reflected by an external object among the emitted light through the light receiver, to obtain a signal generated based on at least a portion of the reflected light and corresponding to the external object, to output guide information related to a location of the external object when the signal satisfies a first designated condition, and to obtain biometric information about the external object when the signal satisfies a second designated condition.

In accordance with another aspect of the present disclosure, a method of measuring biometric information using an electronic device includes emitting light to the outside of the electronic device through at least one light emitter; obtaining light reflected by an external object among the emitted light through a light receiver; obtaining a signal generated based on at least a portion of the reflected light and corresponding to the external object; outputting, when the signal satisfies a first designated condition, guide information related to a location of the external object; and obtaining, when the signal satisfies a second designated condition, biometric information about the external object.

In accordance with another aspect of the present disclosure, there is provided a computer-readable recording medium in which a program is recorded that, when executed by a processor of an electronic device, causes the electronic device to perform a method including operations of: emitting light to the outside of the electronic device through at least one light emitter; obtaining light reflected by an external object among the emitted light through alight receiver; obtaining a signal generated based on at least a portion of the reflected light and corresponding to the external object; outputting guide information related to a location of the external object, when the signal satisfies a first designated condition; and obtaining biometric information about the external object, when the signal satisfies a second designated condition.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
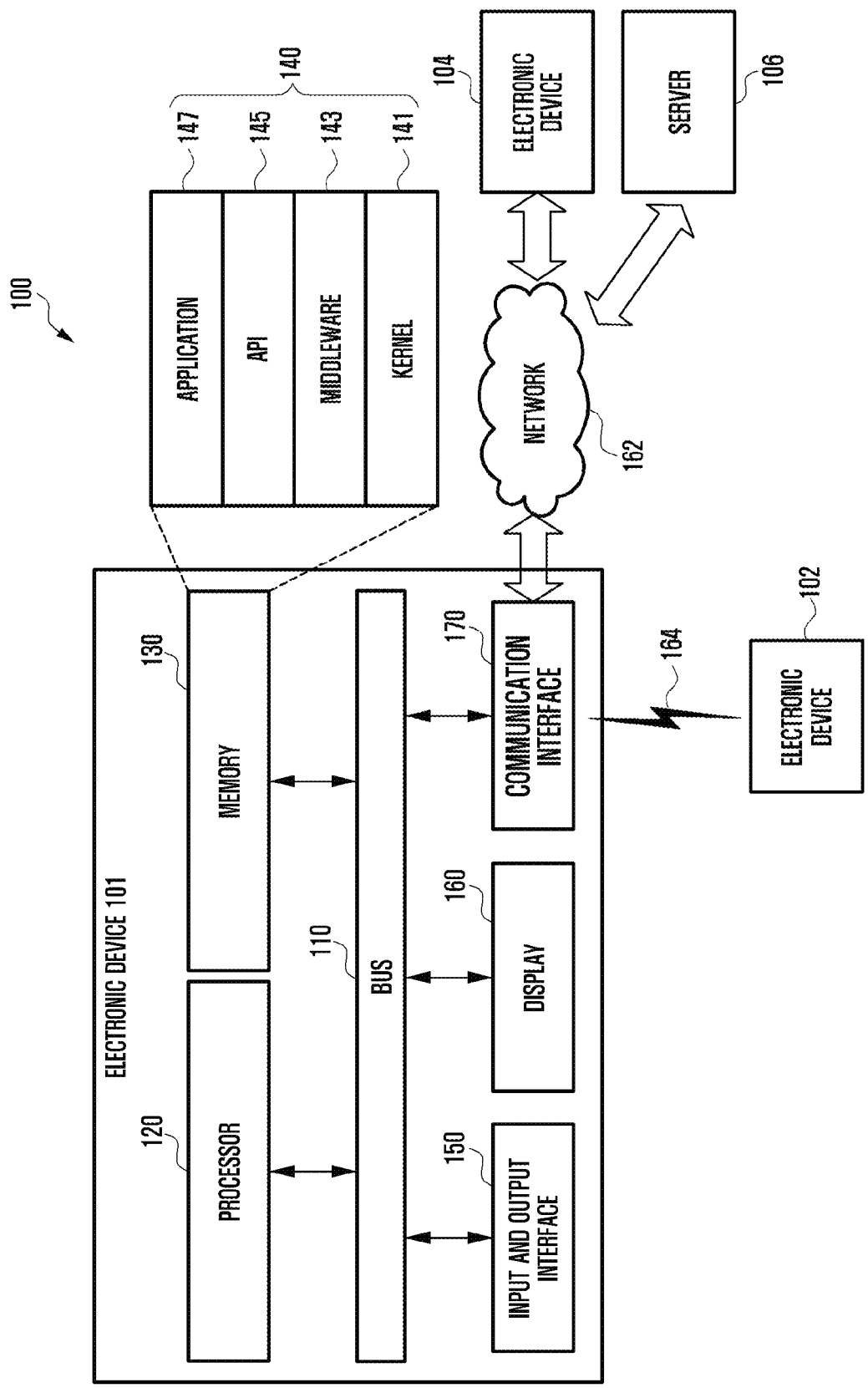
FIG. 1 is a block diagram illustrating a network environment including an electronic device according to various exemplary embodiments of the present disclosure.

FIGS. 1 through 19, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terms "have," "may have," "include," and "may include" as used herein indicate the presence of corresponding features (for example, elements such as numerical values, functions, operations, or parts), and do not preclude the presence of additional features.

The terms "A or B," "at least one of A or/and B," or "one or more of A or/and B" as used herein include all possible combinations of items enumerated with them. For example, "A or B," "at least one of A and B," or "at least one of A or B" means (1) including at least one A, (2) including at least one B, or (3) including both at least one A and at least one B.

The terms such as "first" and "second" as used herein may modify various elements regardless of an order and/or importance of the corresponding elements, and do not limit the corresponding elements. These terms may be used for the purpose of distinguishing one element from another element. For example, a first user device and a second user device may indicate different user devices regardless of the order or importance. For example, a first element may be referred to as a second element without departing from the scope the present disclosure, and similarly, a second element may be referred to as a first element.

It will be understood that, when an element (for example, a first element) is "(operatively or communicatively) coupled with/to" or "connected to" another element (for example, a second element), the element may be directly coupled with/to another element, and there may be an intervening element (for example, a third element) between the element and another element. To the contrary, it will be understood that, when an element (for example, a first element) is "directly coupled with/to" or "directly connected to" another element (for example, a second element), there is no intervening element (for example, a third element) between the element and another element.

The expression "configured to (or set to)" as used herein may be used interchangeably with "suitable for," "having the capacity to," "designed to," "adapted to," "made to," or "capable of" according to a context. The term "configured to (set to)" does not necessarily mean "specifically designed to" in a hardware level. Instead, the expression "apparatus configured to . . . " may mean that the apparatus is "capable of . . . " along with other devices or parts in a certain context. For example, "a processor configured to (set to) perform A, B, and C" may mean a dedicated processor (e.g., an embedded processor) for performing a corresponding operation, or a generic-purpose processor (e.g., a central processing unit (CPU) or an application processor) capable of performing a corresponding operation by executing one or more software programs stored in a memory device.

The terms used in describing various embodiments of the present disclosure are for the purpose of describing particular embodiments and are not intended to limit the present disclosure. As used herein, the singular forms are intended to include the plural forms as well, unless the context clearly indicates otherwise. All of the terms used herein including technical or scientific terms have the same meanings as those generally understood by an ordinary skilled person in the related art unless they are defined otherwise. The terms defined in a generally used dictionary should be interpreted as having the same or similar meanings as the contextual meanings of the relevant technology and should not be interpreted as having ideal or exaggerated meanings unless they are clearly defined herein. According to circumstances, even the terms defined in this disclosure should not be interpreted as excluding the embodiments of the present disclosure.

Electronic devices according to embodiments of the present disclosure may include at least one of, for example, smart phones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to an embodiment of the present disclosure, the wearable devices may include at least one of accessory-type wearable devices (e.g., watches, rings, bracelets, anklets, necklaces, glasses, contact lenses, or head-mounted-devices (HMDs)), fabric or clothing integral wearable devices (e.g., electronic clothes), body-mounted wearable devices (e.g., skin pads or tattoos), or implantable wearable devices (e.g., implantable circuits).

The electronic devices may be smart home appliances. The smart home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ and PlayStation™), electronic dictionaries, electronic keys, camcorders, or electronic picture frames.

The electronic devices may include at least one of various medical devices (e.g., various portable medical measurement devices (such as blood glucose meters, heart rate monitors, blood pressure monitors, or thermometers, and the like), a magnetic resonance angiography (MRA) device, a magnetic resonance imaging (MRI) device, a computed tomography (CT) device, scanners, or ultrasonic devices, and the like), navigation devices, global positioning system (GPS) receivers, event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller machines (ATMs), points of sales (POSs) devices, or Internet of Things (IoT) devices (e.g., light bulbs, various sensors, electric or gas meters, sprinkler devices, fire alarms, thermostats, street lamps, toasters, exercise equipment, hot water tanks, heaters, boilers, and the like).

The electronic devices may further include at least one of parts of furniture or buildings/structures, electronic boards, electronic signature receiving devices, projectors, or various measuring instruments (such as water meters, electricity meters, gas meters, or wave meters, and the like). The electronic devices may be one or more combinations of the above-mentioned devices. The electronic devices may be flexible electronic devices. Also, the electronic devices are not limited to the above-mentioned devices, and may include new electronic devices according to the development of new technologies.

Hereinafter, electronic devices according to various embodiments of the present disclosure will be described with reference to the accompanying drawings. The term "user" as used herein may refer to a person who uses an electronic device or may refer to a device (e.g., an artificial intelligence electronic device) which uses an electronic device.

FIG. 1 illustrates a network environment including an electronic device according to an embodiment of the present disclosure.

Referring to FIG. 1, a network environment 100 includes an electronic device 101 having a bus 110, a processor 120, a memory 130, an input/output interface 150, a display 160, and a communication interface 170. At least one of the above described components may be omitted from the electronic device 101 or another component may be further included in the electronic device 101.

The bus 110 may be a circuit connecting the above described components 120, 130, and 150-170 and transmitting communications (e.g., control messages and/or data) between the above described components.

The processor 120 may include one or more of a CPU, an application processor (AP), and a communication processor (CP). The processor 120 is capable of controlling at least one of other components of the electronic device 101 and/or processing data or operations related to communication.

The memory 130 may include volatile memory and/or non-volatile memory. The memory 130 is capable of storing data or commands related to at least one of other components of the electronic device 101. The memory 130 is capable of storing software and/or a program module 140. For example, the program 140 may include a kernel 141, middleware 143, an application programming interface (API) 145, application programs (or applications) 147, etc. The kernel 141, the middleware 143 or at least part of the API 145 may be called an operating system (OS).

The kernel 141 is capable of controlling or managing system resources (e.g., the bus 110, the processor 120, the memory 130, etc.) used to execute operations or functions of other programs (e.g., the middleware 143, the API 145, and the application programs 147). The kernel 141 provides an interface capable of allowing the middleware 143, the API 145, and the application programs 147 to access and control/manage the individual components of the electronic device 101.

The middleware 143 may be an interface between the API 145 or the application programs 147 and the kernel 141 so that the API 145 or the application programs 147 can communicate with the kernel 141 and exchange data therewith. The middleware 143 is capable of processing one or more task requests received from the application programs 147 according to the priority. For example, the middleware 143 is capable of assigning a priority for use of system resources of the electronic device 101 (e.g., the bus 110, the processor 120, the memory 130, etc.) to at least one of the application programs 147. For example, the middleware 143 processes one or more task requests according to a priority assigned to at least one application program, thereby performing scheduling or load balancing for the task requests.

The API 145 may be an interface that is configured to allow the application programs 147 to control functions provided by the kernel 141 or the middleware 143. The API 145 may include at least one interface or function (e.g., instructions) for file control, window control, image process, text control, or the like.

The input/output interface 150 is capable of transferring instructions or data, received from the user or external devices, to one or more components of the electronic device 101. The input/output interface 150 is capable of outputting instructions or data, received from one or more components of the electronic device 101, to the user or external devices.

The display 160 may include a liquid crystal display (LCD), a flexible display, a transparent display, a light emitting diode (LED) display, an organic LED (OLED) display, micro-Electro-mechanical systems (MEMS) display, an electronic paper display, etc. The display 160 is capable of displaying various types of content (e.g., texts, images, videos, icons, symbols, etc.). The display 160 may also be implemented with a touch screen. In this case, the display 160 is capable of receiving touches, gestures, proximity inputs or hovering inputs, via a stylus pen, or a user's body.

The communication interface 170 is capable of establishing communication between the electronic device 101 and an external device For example, the communication interface 170 is capable of communicating with an external device connected to a network 162 via wired or wireless communication.

Wireless communication may employ, as cellular communication protocol, at least one of long-term evolution (LTE), LTE Advance (LTE-A), code division multiple access (CDMA), wideband CDMA (WCDMA), universal mobile telecommunications system (UMTS), wireless broadband (WiBro), and global system for mobile communication (GSM). Wireless communication may also include short-wireless communication 164. Short-wireless communication 164 may include at least one of wireless fidelity (Wi-Fi), Bluetooth (BT), near field communication (NFC), magnetic secure transmission (MST), and global navigation satellite system (GNSS). The GNSS may include at least one of GPS, global navigation satellite system (Glonass), Beidou NSS (Beidou), Galileo, the European global satellite-based navigation system, according to GNSS using areas, bandwidths, etc. In the present disclosure, "GPS" and "GNSS" may be used interchangeably. Wired communication may include at least one of universal serial bus (USB), high definition multimedia interface (HDMI), recommended standard 232 (RS-232), and plain old telephone service (POTS). The network 162 may include at least one of the following: a telecommunications network, e.g., a computer network (e.g., local area network (LAN) or wide area network (WAN)), the Internet, and a telephone network.

A first external electronic device 102 and a second external electronic device 104 are each identical to or different from the electronic device 101, in terms of type. According to an embodiment, a server 106 is capable of including a group of one or more servers. According to various embodiments, part or all of the operations executed on the electronic device 101 may be executed on another electronic device or a plurality of other electronic devices (e.g., electronic devices 102 and 104 or a server 106). According to an embodiment, when the electronic device needs to perform a function or service automatically or according to a request, it does not perform the function or service, but is capable of additionally requesting at least part of the function related to the function or service from another electronic device (e.g., electronic devices 102 and 104 or a server 106). The other electronic device (e.g., electronic devices 102 and 104 or a server 106) is capable of executing the requested function or additional functions, and transmitting the result to the electronic device 101. The electronic device 101 processes the received result, or further proceeds with additional processes, to provide the requested function or service. To this end, the electronic device 101 may employ cloud computing, distributed computing, or client-server computing technology.

Figure 2:
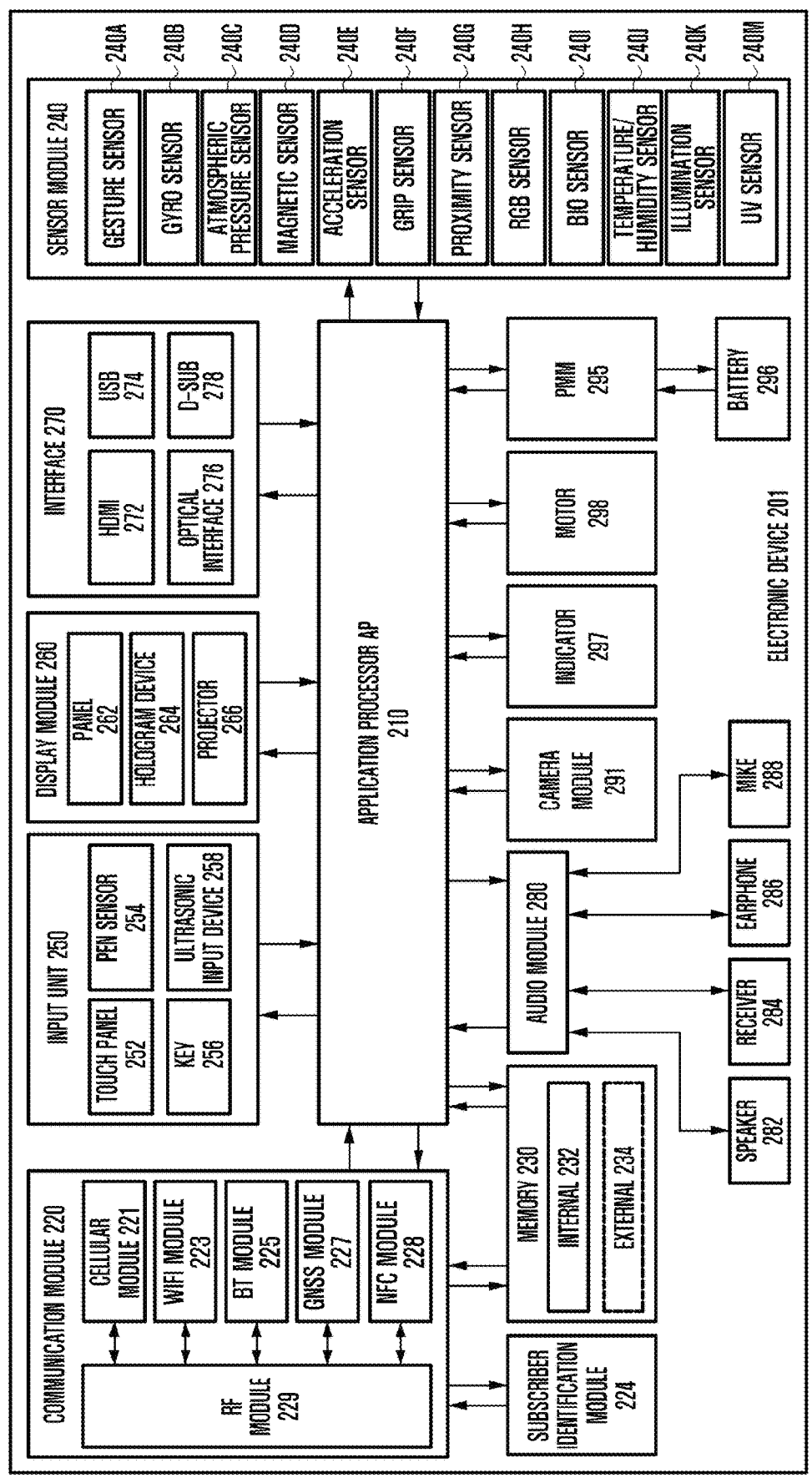
FIG. 2 is a block diagram illustrating a configuration of an electronic device according to various exemplary embodiments of the present disclosure.

FIG. 2 is a block diagram showing a configuration of an electronic device according to an embodiment of the present disclosure.

Referring to FIG. 2, an electronic device 201 may include a part or all of the components in the electronic device 101 shown in FIG. 1. The electronic device 201 may include one or more processors 210 (e.g., APs), a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 is capable of driving, for example, an operating system or an application program to control a plurality of hardware or software components connected to the processor 210, processing various data, and performing operations. The processor 210 may be implemented as, for example, a system on chip (SoC). The processor 210 may further include a graphic processing unit (GPU) and/or an image signal processor. The processor 210 may also include at least part of the components shown in FIG. 2, e.g., a cellular module 221. The processor 210 is capable of loading commands or data received from at least one of other components (e.g., a non-volatile memory) on a volatile memory, processing the loaded commands or data. The processor 210 is capable of storing various data in a non-volatile memory.

The communication module 220 may include the same or similar configurations as the communication interface 170 shown in FIG. 1. For example, the communication module 170 is capable of including the cellular module 221, a Wi-Fi module 223, a Bluetooth (BT) module 225, a GNSS module 227 (e.g., a GPS module, Glonass module, Beidou module or Galileo module), an NFC module 228, and a radio frequency (RF) module 229.

The cellular module 221 is capable of providing a voice call, a video call, an SMS service, an Internet service, etc., through a communication network, for example. The cellular module 221 is capable of identifying and authenticating an electronic device 201 in a communication network by using the SIM 224. The cellular module 221 is capable of performing at least a part of the functions provided by the processor 210. The cellular module 221 may include a CP.

Each of the Wi-Fi module 223, the BT module 225, the GNSS module 227, and the NFC module 228 may include a processor for processing data transmitted or received through the corresponding module. At least part of the cellular module 221, Wi-Fi module 223, BT module 225, GNSS module 227, and NFC module 228 (e.g., two or more modules) may be included in one integrated chip (IC) or one IC package.

The RF module 229 is capable of transmission/reception of communication signals, e.g., RF signals. The RF module 229 is capable of including a transceiver, a power amplifier module (PAM), a frequency filter, a low noise amplifier (LNA), an antenna, etc. At least one of the cellular module 221, the Wi-Fi module 223, the BT module 225, the GNSS module 227, and the NFC module 228 is capable of transmission/reception of RF signals through a separate RF module.

The memory 230 may include a built-in memory 232 or an external memory 234. The built-in memory 232 is capable of including at least one of a volatile memory, e.g., a dynamic random access memory (DRAM), a static RAM (SRAM), a synchronous dynamic RAM (SDRAM), etc. and a non-volatile memory, e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, an NOR flash memory, etc.), a hard drive, a solid state drive (SSD), etc.

The external memory 234 may include a flash drive, e.g., a compact flash (CF), a secure digital (SD), a micro secure digital (Micro-SD), a mini secure digital (Mini-SD), an extreme digital (xD), a multi-media card (MMC), a memory stick, etc. The external memory 234 may be connected to the electronic device 201, functionally and/or physically, through various interfaces.

The sensor module 240 is capable of measuring/detecting a physical quantity or an operation state of the electronic device 201, and converting the measured or detected information into an electronic signal. The sensor module 240 may include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., a red, green and blue (RGB) sensor), a biometric sensor 240I, a temperature/humidity sensor 240J, an illuminance sensor 240K, and a ultraviolet (UV) sensor 240M. Additionally or alternatively, the sensor module 240 may also include an e-nose sensor, an electromyography (EMG) sensor, an electroencephalogram (EEG) sensor, an electrocardiogram (ECG) sensor, an infrared (IR) sensor, an iris sensor and/or a fingerprint sensor. The sensor module 240 may further include a control circuit for controlling one or more sensors included therein. The electronic device 201 may include a processor, configured as part of the processor 210 or a separate component, for controlling the sensor module 240. In this case, while the processor 210 is operating in sleep mode, the processor is capable of controlling the sensor module 240.

The input device 250 may include a touch panel 252, a (digital) pen sensor 254, a key 256, or an ultrasonic input unit 258. The touch panel 252 may be implemented with at least one of a capacitive touch system, a resistive touch system, an infrared touch system, and an ultrasonic touch system. The touch panel 252 may further include a control circuit, and the touch panel 252 may include a tactile layer to provide a tactile response to the user. The (digital) pen sensor 254 may be implemented with a part of the touch panel or with a separate recognition sheet. The key 256 may include a physical button, an optical key, or a keypad. The ultrasonic input unit 258 is capable of detecting ultrasonic waves, created in an input tool, through a microphone 288, and identifying data corresponding to the detected ultrasonic waves.

The display 260 may include a panel 262, a hologram unit 264, or a projector 266. The panel 262 may include the same or similar components as the display 160 shown in FIG. 1. The panel 262 may be implemented to be flexible, transparent, or wearable. The panel 262 may also be incorporated into one module together with the touch panel 252. The hologram unit 264 is capable of showing a stereoscopic image in the air by using light interference. The projector 266 is capable of displaying an image by projecting light onto a screen. The screen may be located inside or outside of the electronic device 201. The display 260 may further include a control circuit for controlling the panel 262, the hologram unit 264, or the projector 266.

The interface 270 may include an HDMI 272, a USB 274, an optical interface 276, or a d-subminiature (D-sub) 278.

The interface 270 may be included in the communication interface 170 shown in FIG. 1. Additionally or alternatively, the interface 270 may include a mobile high-definition link (MHL) interface, a SD card/MMC interface, or an infrared data association (IrDA) standard interface.

The audio module 280 is capable of providing bidirectional conversion between a sound and an electronic signal. At least part of the components in the audio module 280 may be included in the input/output interface 150 shown in FIG. 1. The audio module 280 is capable of processing sound information input or output through a speaker 282, a receiver 284, earphones 286, a microphone 288, etc.

The camera module 291 is a device capable of taking both still and moving images. The camera module 291 may include one or more image sensors (e.g., a front image sensor or a rear image sensor), a lens, an image signal processor (ISP), a flash (e.g., an LED or xenon lamp), etc.

The power management module 295 is capable of managing power of the electronic device 201. The power management module 295 may include a power management integrated circuit (PMIC), a charger IC, or a battery gauge. The PMIC may employ wired charging and/or wireless charging methods. Examples of the wireless charging method are magnetic resonance charging, magnetic induction charging, and electromagnetic charging. To this end, the PMIC may further include an additional circuit for wireless charging, such as a coil loop, a resonance circuit, a rectifier, etc. The battery gauge is capable of measuring the residual capacity, charge in voltage, current, or temperature of the battery 296.

The battery 296 takes the form of either a rechargeable battery or a solar battery.

The indicator 297 is capable of displaying a specific status of the electronic device 201 or a part thereof (e.g., the processor 210), e.g., a boot-up status, a message status, a charging status, etc. The motor 298 is capable of converting an electrical signal into mechanical vibrations, such as, a vibration effect, a haptic effect, etc. The electronic device 201 may also include a processing unit (e.g., GPU) for supporting a mobile TV. The processing unit for supporting a mobile TV is capable of processing media data pursuant to standards, e.g., digital multimedia broadcasting (DMB), digital video broadcasting (DVB), or mediaFlo™, etc.

Figure 3:
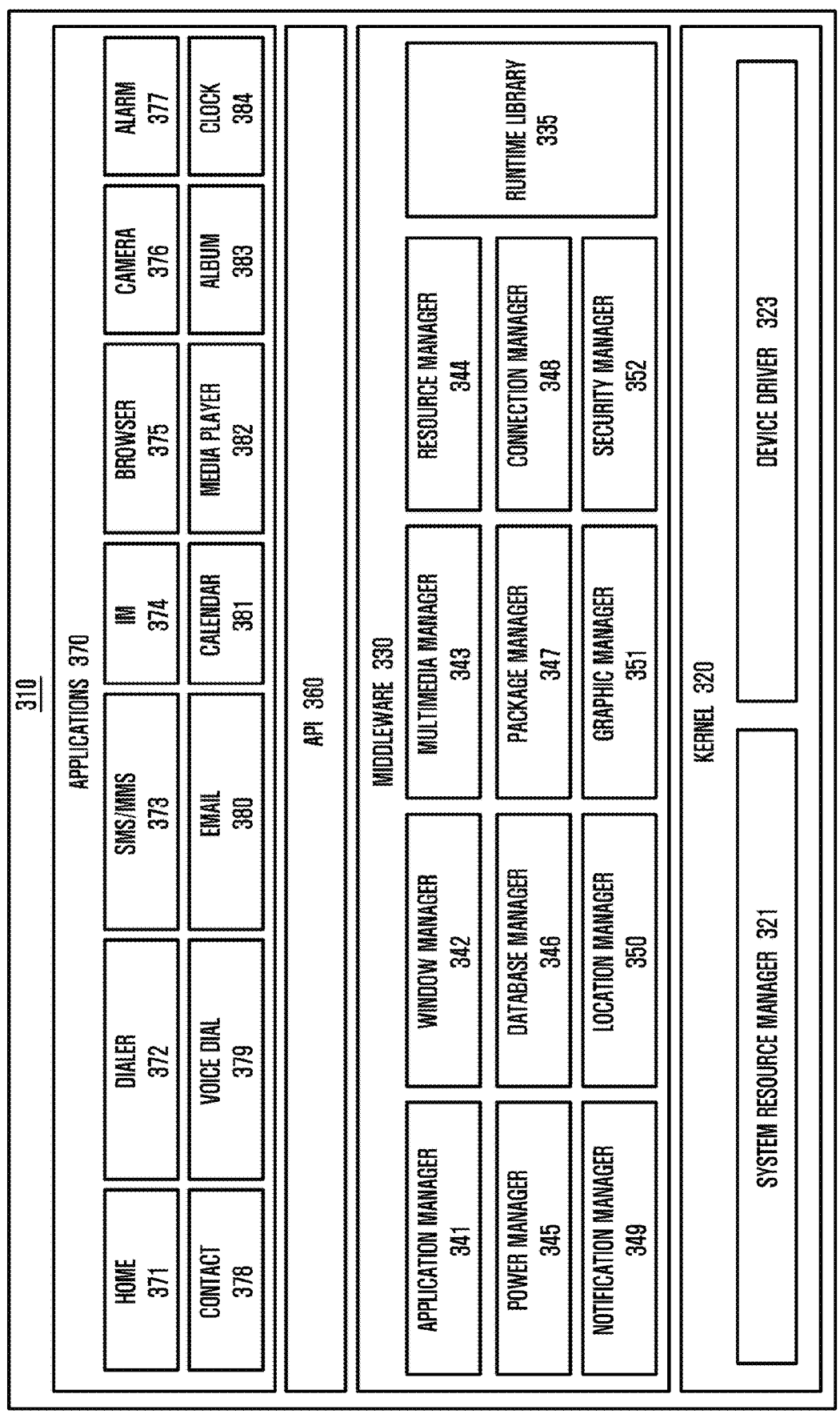
FIG. 3 is a block diagram illustrating a configuration of a program module according to various exemplary embodiments of the present disclosure.

FIG. 3 is a block diagram of a programming module according to an embodiment of the present disclosure.

Referring to FIG. 3, a program module 310 (e.g., program module 140 shown in FIG. 1) is capable of including an OS for controlling resources related to the electronic device (e.g., electronic device 101) and/or various applications (e.g., application programs 147 shown in FIG. 1) running on the OS. The OS may be Android, iOS, Windows, Symbian, Tizen, Bada, etc.

The program module 310 is capable of including a kernel 320, middleware 330, an API 360 and/or applications 370. At least part of the program module 310 may be preloaded on the electronic device or downloaded from a server (e.g., an electronic device 102 or 104, server 106, etc.).

The kernel 320 (for example, kernel 141) may include a system resource manager 321 and/or a device driver 323. The system resource manager 321 may include, for example, a process manager, a memory manager, and a file system manager. The system resource manager 321 may perform a system resource control, allocation, and recall. The device driver 323 may include, for example, a display driver, a camera driver, a Bluetooth driver, a shared memory driver, a USB driver, a keypad driver, a Wi-Fi driver, and an audio driver. Further, according to an embodiment, the device driver 323 may include an Inter-Process Communication (IPC) driver.

The middleware 330 may provide a function required in common by the applications 370. Further, the middleware 330 may provide a function through the API 360 to allow the applications 370 to efficiently use limited system resources within the electronic device. According to an embodiment, the middleware 330 (for example, the middleware 143) may include at least one of a runtime library 335, an application manager 341, a window manager 342, a multimedia manager 343, a resource manager 344, a power manager 345, a database manager 346, a package manager 347, a connection manager 348, a notification manager 349, a location manager 350, a graphic manager 351, and a security manager 352. Furthermore, although not shown, the middleware 330 may also include a payment manager.

The runtime library 335 may include, for example, a library module used by a complier to add a new function through a programming language while the applications 370 are executed. According to an embodiment, the runtime library 335 executes input and output, management of a memory, a function associated with an arithmetic function and the like.

The application manager 341 may manage, for example, a life cycle of at least one of the applications 370. The window manager 342 may manage GUI resources used on the screen. The multimedia manager 343 may detect a format required for reproducing various media files and perform an encoding or a decoding of a media file by using a codec suitable for the corresponding format. The resource manager 344 manages resources such as a source code, a memory, or a storage space of at least one of the applications 370.

The power manager 345 may operate together with a basic input/output system (BIOS) to manage a battery or power and provides power information required for the operation. The database manager 346 may manage generation, search, and change of a database to be used by at least one of the applications 370. The package manager 347 may manage an installation or an update of an application distributed in a form of a package file.

The connection manager 348 may manage, for example, a wireless connection such as Wi-Fi or Bluetooth. The notification manager 349 may display or notify a user of an event such as an arrival message, an appointment, a proximity alarm or the like, in a manner that does not disturb the user. The location manager 350 may manage location information of the electronic device. The graphic manager 351 may manage a graphic effect provided to the user or a user interface related to the graphic effect. The security manager 352 provides a general security function required for a system security or a user authentication. According to an embodiment, when the electronic device (for example, the electronic device 101) has a call function, the middleware 330 may further include a telephony manager for managing a voice of the electronic device or a video call function.

The middleware 330 is capable of including modules configuring various combinations of functions of the above described components. The middleware 330 is capable of providing modules specialized according to types of operation systems to provide distinct functions. The middleware 330 may be adaptively configured in such a way as to remove part of the existing components or to include new components.

The API 360 (for example, API 145) may be a set of API programming functions, and may be provided with a different configuration according to an operating system. For example, in Android or iOS, a single API set may be provided for each platform. In Tizen, two or more API sets may be provided.

The applications 370 (e.g., application programs 147) may include one or more applications for performing various functions, e.g., home 371, dialer 372, short message service (SMS)/multi-media message service (MMS) 373, instant message (IM) 374, browser 375, camera 376, alarm 377, contact 378, voice dial 379, email 380, calendar 381, media player 382, album 383, and clock 384. Furthermore, although not shown, the applications 370 may also include health care (e.g., an application for measuring amount of exercise, blood sugar level, etc.), and environment information (e.g., an application for providing atmospheric pressure, humidity, temperature, etc.).

According to an embodiment, the applications 370 are capable of including an application for supporting information exchange between an electronic device (e.g., electronic device 101) and an external device (e.g., electronic devices 102 and 104), which is hereafter called 'information exchange application'). The information exchange application is capable of including a notification relay application for relaying specific information to external devices or a device management application for managing external devices.

According to an embodiment, the applications 370 are capable of including an application (e.g., a health care application of a mobile medical device, etc.) having specified attributes of an external device (e.g., electronic devices 102 and 104). According to an embodiment, the applications 370 are capable of including applications received from an external device (e.g., a server 106, electronic devices 102 and 104). According to an embodiment, the applications 370 are capable of including a preloaded application or third party applications that can be downloaded from a server. It should be understood that the components of the program module 310 may be called different names according to types of operating systems.

The term "module" according to the embodiments of the disclosure, means, but is not limited to, a unit of one of software, hardware, and firmware or any combination thereof. The term "module" may be used interchangeably with the terms "unit," "logic," "logical block," "component," or "circuit." The term "module" may denote a smallest unit of component or a part thereof. The term "module" may be the smallest unit of performing at least one function or a part thereof. A module may be implemented mechanically or electronically. For example, a module may include at least one of application-specific integrated circuit (ASIC) chip, field-programmable gate arrays (FPGAs), and Programmable-Logic Device known or to be developed for certain operations.

According to various embodiments of the present disclosure, the devices (e.g. modules or their functions) or methods may be implemented by computer program instructions stored in a computer-readable storage medium. In the case that the instructions are executed by at least one processor (e.g. processor 120), the at least one processor may execute the functions corresponding to the instructions. The computer-readable storage medium may be the memory 130. At least a part of the programming module may be implemented (e.g. executed) by the processor 120. At least a part of the programming module may include modules, programs, routines, sets of instructions, and processes for executing the at least one function.

The computer-readable storage medium includes magnetic media such as a floppy disk and a magnetic tape, optical media including a compact disc (CD) ROM and a DVD ROM, a magneto-optical media such as a floptical disk, and the hardware device designed for storing and executing program commands such as ROM, RAM, and flash memory. The program commands include the language code executable by computers using the interpreter as well as the machine language codes created by a compiler. The aforementioned hardware device can be implemented with one or more software modules for executing the operations of the various embodiments of the present disclosure.

The module or programming module of the present disclosure may include at least one of the aforementioned components with omission of some components or addition of other components. The operations of the modules, programming modules, or other components may be executed in series, in parallel, recursively, or heuristically. Also, some operations may be executed in different order, omitted, or extended with other operations.

Figure 4:
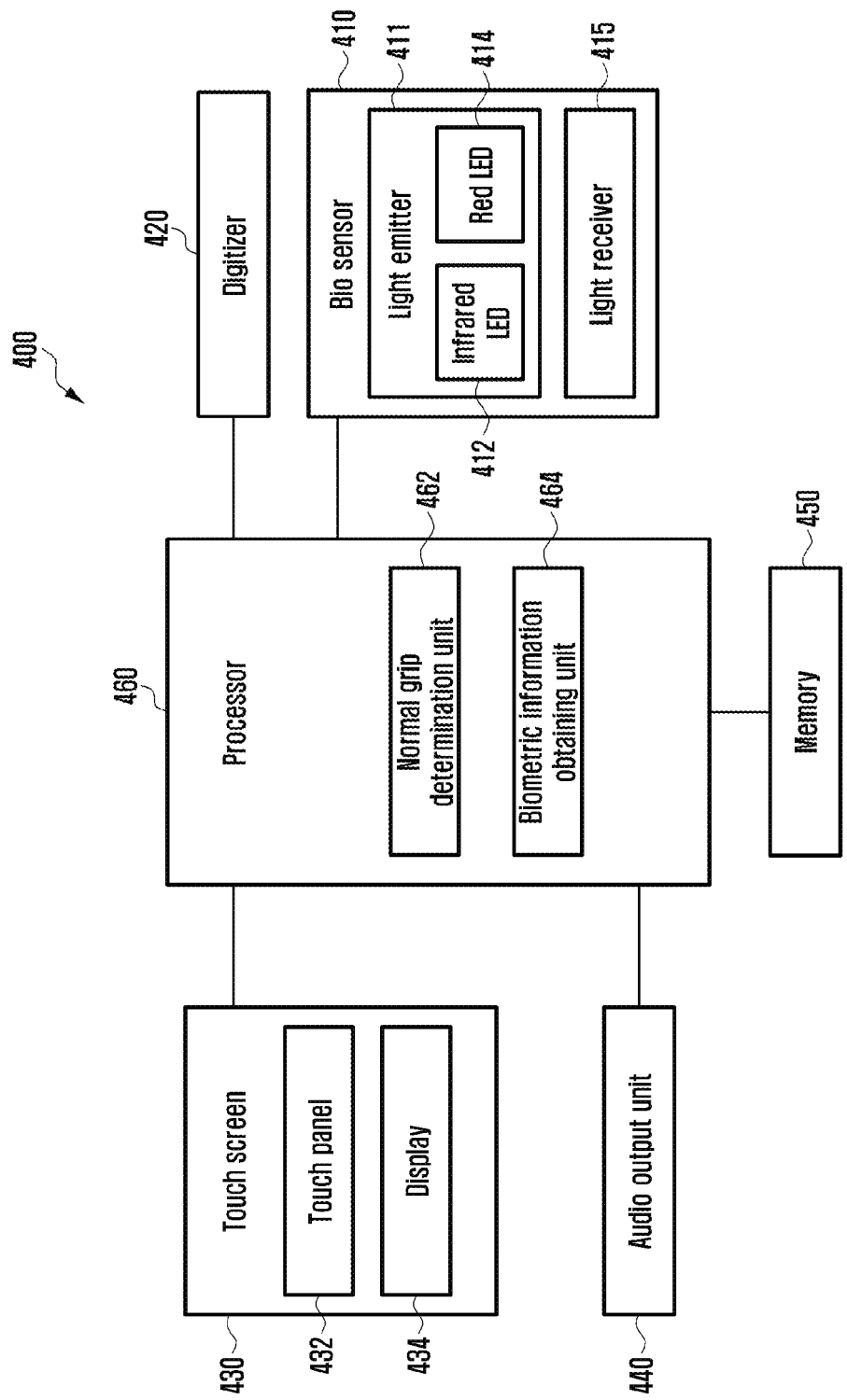
FIG. 4 is a block diagram illustrating a configuration of an electronic device according to various exemplary embodiments of the present disclosure.

FIG. 4 is a block diagram illustrating a configuration of an electronic device according to various exemplary embodiments of the present disclosure.

With reference to FIG. 4, an electronic device 400 according to various exemplary embodiments of the present disclosure may include a bio sensor 410, digitizer 420, touch screen 430, audio output unit 440, memory 450, and processor 460.

The electronic device 400 may include, for example, a portion or the entire of the electronic devices 101, 102, and 104 of FIG. 1 or the electronic device 201 of FIG. 2. The electronic device 400 may include at least one of a smart phone, tablet personal computer (PC), and wearable device.

The bio sensor 410 may include the entire or a portion (e.g., the bio sensor 240I) of the sensor module 240 of FIG. 2. The audio output unit 440 may include the audio module 280 of FIG. 2. The memory 450 may include the memory 130 of FIG. 1 or the memory 230 of FIG. 2. The processor 460 may include the processor 120 of FIG. 1 or the processor 210 of FIG. 2.

According to an exemplary embodiment, the bio sensor 410 may include a photoplethysmography (PPG) sensor. The bio sensor 410 may include at least one light emitter 411 and at least one light receiver 415. For example, the bio sensor 410 may output light to a person skin (e.g., blood vessel) through the light emitter 411 and detect light reflected and returned from a person skin (e.g., blood vessel) through the light receiver 415 with a current signal. The bio sensor 410 may measure at least one of a heart rate, oxygen saturation, and stress of a user of the electronic device 400 through a processing of the detected current signal. For example, because the heart rate is measured based on a light quantity reflected from a person skin (e.g., blood vessel) to be returned, for accurate measurement of the heart rate, it may be an important element that a user finger of the electronic device 400 is accurately located at the bio sensor 410.

The at least one light emitter 411 may include at least one of a first light emitter (e.g., infrared (IR) LED) 412, second light emitter (e.g., red LED 414), third light emitter (e.g., green LED) (not shown), and fourth light emitter (e.g., blue LED) (not shown) having different wavelength characteristics. The light emitter 411 may select and use an LED corresponding to an object or an environment for measuring biometric information about a user of the electronic device 400. The electronic device 400 according to various exemplary embodiments of the present disclosure may include the first light emitter (e.g., the IR LED 412) and the second light emitter (e.g., the red LED 414). The light emitter 411 may emit light toward a user body (e.g., finger or wrist) at the outside of the electronic device 400. The light emitter 411 may include an infrared light emitting circuit.

The at least one light receiver 415 may include a photo diode (PD). The light receiver 415 may obtain light reflected from a user skin (e.g., blood vessel) among light emitted from the light emitter 411. The bio sensor 410 may obtain a signal corresponding to a user skin (e.g., blood vessel) based on the light obtained through the light receiver 415. The bio sensor 410 may transfer at least one information related to the light obtained through the light receiver 415 to the processor 460. The light receiver 415 may include an infrared light detection circuit.

According to an exemplary embodiment, the digitizer 420 may be configured at a periphery of the bio sensor 410. When a user finger of the electronic device 400 touches the bio sensor 410, the digitizer 420 may detect location information (e.g., touch coordinate, touch direction, touch angle) and transfer the detected location information to the processor 460.

According to an exemplary embodiment, when the user finger of the electronic device 400 is not accurately located at the bio sensor 410, the touch screen 430 may display a user interface (UI) that guides to move a location of the user finger to accurately locate the user finger at the bio sensor 410.

According to various exemplary embodiments, the touch screen 430 may perform an input function and a display function. For this reason, the touch screen 430 may include a touch panel 432 (e.g., the touch panel 252 of FIG. 2) and a display 434 (e.g., the display 160 of FIG. 1 or the display 260 of FIG. 2). The touch panel 432 may be configured with a touch sensor such as capacitive overlay, resistive overlay, and infrared beam or a pressure sensor. All kinds of sensor devices that can detect a contact or a pressure of an object in addition to the sensors may be configured with the touch panel 432 of the present exemplary embodiment. The touch panel 432 may detect a user touch input and generate a detection signal to transmit the detection signal to the processor 460. The detection signal may include coordinate information, direction information, and touch angle information in which the user touch is input. When the user inputs a moving action of the touch location, the touch panel 432 may generate a detection signal including coordinate information and direction information of a touch location moving path to transmit the detection signal to the processor 460. The display 434 may be formed with a liquid crystal display (LCD), organic light emitting diodes (OLED), or active matrix organic light emitting diodes (AMOLED) and may visually provide a menu, input data, function setup information, and other various information of the electronic device 400 to the user. The display 434 according to various exemplary embodiments of the present disclosure may display an UI that guides the user finger to accurately locate at the bio sensor 410.

According to an exemplary embodiment, when the user finger of the electronic device 400 is not accurately located at the bio sensor 410, the audio output unit 440 may output a guide voice (e.g., Please move the finger to the right. Please move the finger to the left) that guides to move a location of the user finger to accurately locate the user finger at the bio sensor 410. For example, the audio output unit 440 may include a speaker (e.g., the speaker 282 of FIG. 2) for outputting a guide voice or other audio signals stored at the memory 450.

According to an exemplary embodiment, the memory 450 may store a bio signal (including a reference bio signal) of a user body (e.g., a finger or a back of a hand) measured through the light receiver 415 of the bio sensor 410. The memory 450 may store resources on an UI (e.g., graphic object) that guides the user finger to accurately locate at the bio sensor 410. The resources on the UI may be loaded at a framework to be displayed in the display 434. The memory 450 may store a guide voice that guides the user finger to accurately locate at the bio sensor 410. In an exemplary embodiment of the present disclosure, it is described that a reference bio signal of a user of the electronic device 400 has been stored at the memory 450, but a bio signal of the user of the electronic device 400 may be measured in real time through the bio sensor 410 instead of storing the reference bio signal.

According to various exemplary embodiments, the memory 450 may perform a function of storing a program and an operating system (OS) for a processing and the control of the processor 460 and various applications and input/output data and store a program that controls general operations of the electronic device 400. The memory 450 may store various setup information necessary when processing a function in the electronic device 400.

According to an exemplary embodiment, the processor 460 may control a function and operation of the bio sensor 410, the digitizer 420, the touch screen 430, the audio output unit 440, and the memory 450 within the electronic device 400. The processor 460 may control the display 434 to display an UI (e.g., graphic object) that guides a user finger to accurately locate at the bio sensor 410. The processor 460 may output a guide voice that guides a user finger to accurately locate at the bio sensor 410 through the audio output unit 440.

According to an exemplary embodiment, the processor 460 may include a normal grip determination unit 462 and a biometric information obtaining unit 464. The normal grip determination unit 462 may determine whether the user finger of the electronic device 400 has accurately located (e.g., grip) at the bio sensor 410 based on at least one information received from the bio sensor 410. For example, the normal grip determination unit 462 may determine whether a user finger of the electronic device 400 is located at which side of the right or the left based on information obtained by at least one light receiver 415 included in the bio sensor 410. The normal grip determination unit 462 may determine a finger location of a user of the electronic device 400 based on information obtained through the digitizer 420 formed at a periphery of the bio sensor 410. If the user finger is accurately located (e.g., grip) at the bio sensor 410 through the normal grip determination unit 462, the biometric information obtaining unit 464 may obtain biometric information (e.g., heart rate, oxygen saturation, and stress) about the user of the electronic device 400 based on information received through the bio sensor 410.

According to an exemplary embodiment, the processor 460 may emit light to the outside of the electronic device 400 through at least one light emitter 411 (e.g., infrared light emitting circuit). The processor 460 may obtain light reflected by the external object (e.g., finger) among the light emitted from the light emitter 411 through at least one light receiver 415 (e.g., infrared light detection circuit). The processor 460 may obtain a signal generated based on at least a portion of the reflected light and corresponding to the external object (e.g., finger). When the signal satisfies a first designated condition (e.g., a correlation level 1%-50%), the processor 460 may control the display 434 to display guide information related to a location of the external object (e.g., finger) to the light emitter 411 and the light receiver 415. If the signal satisfies a second designated condition (e.g., a correlation level 50%-100%), the processor 460 may be configured to obtain biometric information about the external object (e.g., finger). If the signal satisfies a second designated condition, the processor 460 may store the signal as a reference bio signal of a user of the electronic device 400 at the memory 450.

According to various exemplary embodiments, the processor 460 may perform a function of controlling general operations of the electronic device 400 and a signal flow between internal constituent elements thereof and processing data. The processor 460 may be configured with, for example, a central processing unit (CPU), application processor, and communication processor. The processor 460 may include a processor (e.g., sensor hub) operating with lower power than that of the application processor. The processor 460 may include an application processor and a sensor hub. The processor 460 may be formed with a single core processor or a multi-core processor and may be formed with a plurality of processors.

Figure 5:
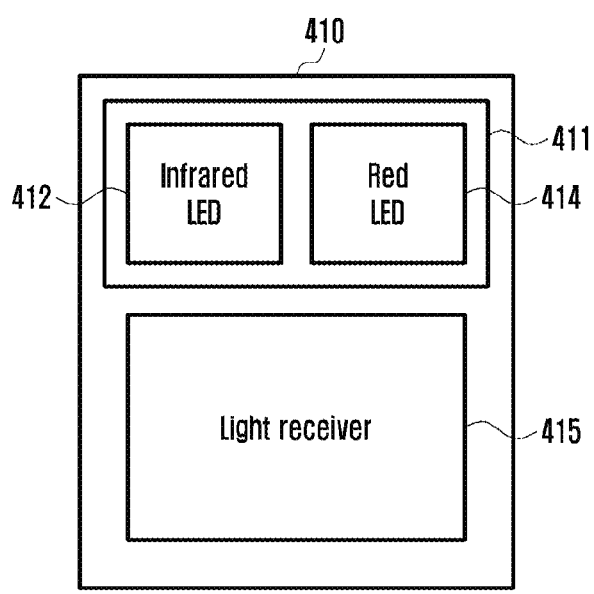
FIG. 5 is a block diagram illustrating a configuration of a bio sensor (e.g., PPG sensor) of an electronic device according to various exemplary embodiments of the present disclosure.

FIG. 5 is a block diagram illustrating a configuration of a bio sensor (e.g., the bio sensor 410 of FIG. 4) of an electronic device according to various exemplary embodiments of the present disclosure.

With reference to FIG. 5, the bio sensor 410 according to various exemplary embodiments of the present disclosure may include at least one light emitter 411 and at least one light receiver 415.

The light emitter 411 may include a first light emitter (e.g., the IR LED 412) and a second light emitter (e.g., the red LED 414) parallel to a first direction (e.g., horizontal direction). According to various exemplary embodiments, the light emitter 411 may include a second light emitter (e.g., the red LED 414) and a first light emitter (e.g., the IR LED 412) parallel to a first direction (e.g., horizontal direction). The light receiver 415 may be disposed in a second direction (e.g., vertical direction) of the light emitter 411. According to another exemplary embodiment, the first light emitter (e.g., the IR LED 412) and the second light emitter (e.g., the red LED 414) included in the light emitter 411 may be disposed at an upper portion or a lower portion, respectively, of the light receiver 415 based on the light receiver 415. According to another exemplary embodiment, the light emitter 411 may further include the first light emitter (e.g., the IR LED 412), the second light emitter (e.g., the red LED 414), a third light emitter (e.g., green LED), and a fourth light emitter (e.g., blue LED). According to another exemplary embodiment, in the light emitter 411, the first light emitter (e.g., the IR LED 412), the second light emitter (e.g., the red LED 414), the third light emitter (e.g., green LED), and the fourth light emitter (e.g., blue LED) may be disposed at an upper portion, lower portion, left side portion, and right side portion, respectively, of the light receiver 415 based on the light receiver 415.

Figure 6A:
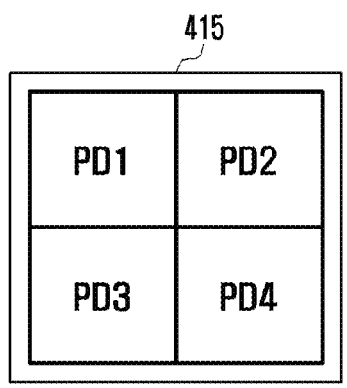
FIGS. 6A-6C are block diagrams illustrating a configuration of a light receiver (e.g., photodiode PD) of an electronic device according to various exemplary embodiments of the present disclosure.
Figure 6B:
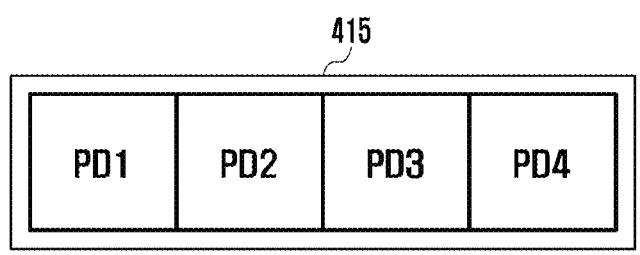
Figure 6C:
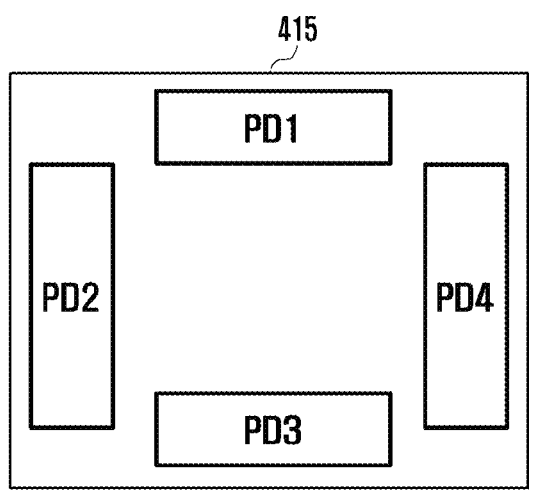

FIGS. 6A-6C are block diagrams illustrating a configuration of a light receiver (e.g., the light receiver 415 of FIG. 4) of an electronic device according to various exemplary embodiments of the present disclosure.

With reference to FIGS. 6A to 6C, the light receiver 415 according to various exemplary embodiments of the present disclosure may include at least one photodiode (e.g., PD1-PD4).

With reference to FIG. 6A, the light receiver 415 may be configured in a form in which a first photodiode PD1 to a fourth photodiode PD4 are integrated.

With reference to FIG. 6B, the light receiver 415 may be configured in a form in which the first photodiode PD1 to the fourth photodiode PD4 are disposed parallel to a first direction (e.g., a horizontal direction). According to various exemplary embodiments, the light receiver 415 may be configured in a form in which the first photodiode PD1 to the fourth photodiode PD4 are disposed parallel to a second direction (e.g., a vertical direction).

With reference to FIG. 6C, the light receiver 415 may be configured in a form in which the first photodiode PD1 to the fourth photodiode PD4 are disposed at an upper portion, left side portion, lower portion, and right side portion, respectively, based on a central hole.

According to an exemplary embodiment, as shown in FIG. 6C, the normal grip determination unit 462 of the processor 460 may determine a finger grip location of a user of the electronic device 400 based on a signal received through the light receiver 415 in which the first photodiode PD1 to the fourth photodiode PD4 are disposed at an upper portion, left side portion, lower portion, and right side portion, respectively, based on a central hole. The light emitter 411 according to various exemplary embodiments of the present disclosure may be disposed at the center of the light receiver 415 in which the first photodiode PD1 to the fourth photodiode PD4 are disposed at an upper portion, left side portion, lower portion, and right side portion, respectively.

Figure 7:
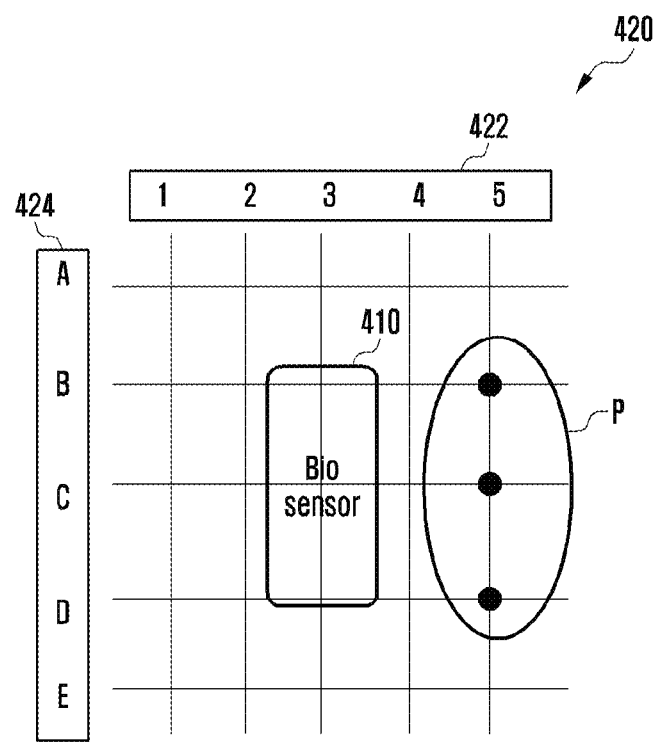
FIG. 7 is a diagram illustrating an example of determining a grip location of a user finger through a digitizer formed at a periphery of a bio sensor of an electronic device according to various exemplary embodiments of the present disclosure.

FIG. 7 is a diagram illustrating an example of determining a user finger grip location through a digitizer (e.g., the digitizer 420 of FIG. 4) formed at a periphery of a bio sensor of an electronic device according to various exemplary embodiments of the present disclosure.

With reference to FIG. 7, the digitizer 420 according to various exemplary embodiments of the present disclosure may be formed at a periphery of the bio sensor 410. The digitizer 420 may include a first driver 422 (e.g., data driver) and a second driver 424 (e.g., gate driver).

With reference to FIG. 7, for example, when a location of the bio sensor 410 is determined to 3B, 3C, and 3D of the first driver 422 and the second driver 424 and when a finger grip location P of a user of the electronic device 400 to the bio sensor 410 is determined to 5B, 5C, and 5D of the first driver 422 and the second driver 424, the processor 460 may determine that a finger grip location P of the user of the electronic device 400 is not located at a location corresponding to the bio sensor 410 and display an UI that guides to normally move the user's finger location. For example, the digitizer 420 may detect a finger grip location P of the user of the electronic device 400 and transfer information about the detected finger grip location to the processor 460. In this case, the processor 460 may output an UI (e.g., graphic object) or a guide voice that guides a finger grip location of the user to accurately locate at the bio sensor 410 through the display 434 or the audio output unit 440.

Figure 8A:
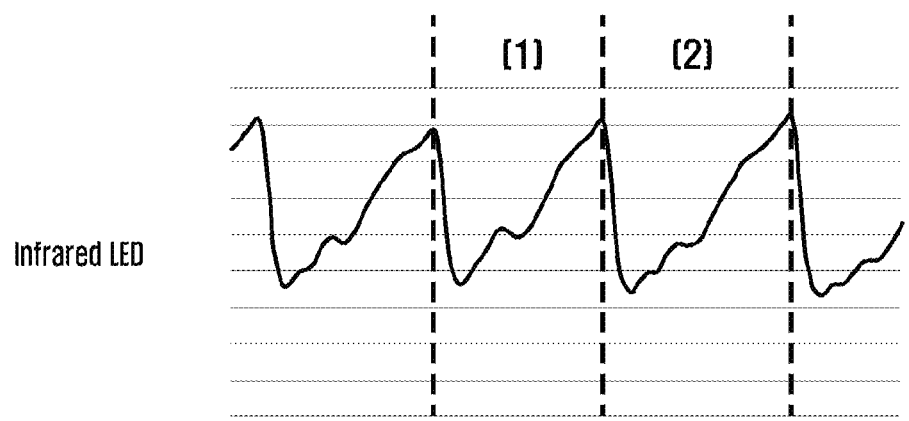
FIGS. 8A-8B are diagrams illustrating an example of determining whether a user normally grips a bio sensor through a normal grip determination unit of an electronic device according to various exemplary embodiments of the present disclosure.
Figure 8B:
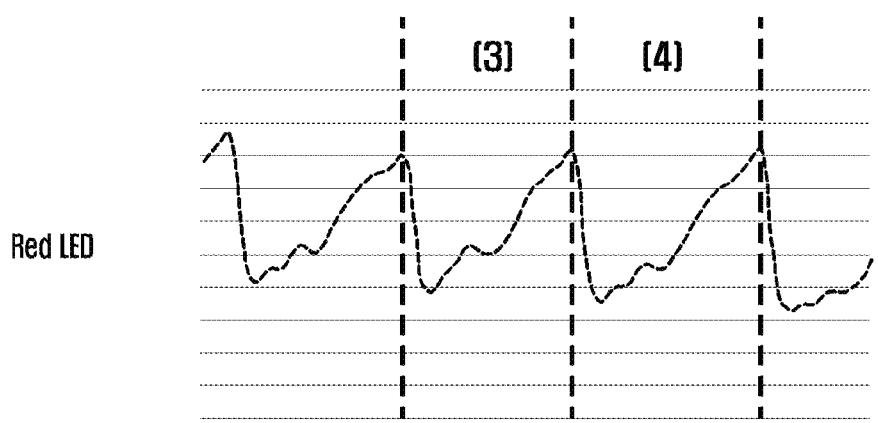

FIGS. 8A-8B are diagrams illustrating an example of determining whether a user normally grips a bio sensor (e.g., the bio sensor 410 of FIG. 4) through a normal grip determination unit (e.g., the normal grip determination unit 462 of FIG. 4) of an electronic device according to various exemplary embodiments of the present disclosure.

FIG. 8A illustrates a signal (e.g., waveform) obtained through the first light emitter (e.g., the IR LED 412) of the light emitter 411 and the light receiver 415, and FIG. 8B illustrates a signal (e.g., waveform) obtained through the second light emitter (e.g., the red LED 414) of the light emitter 411 and the light receiver 415.

With reference to FIGS. 8A and 8B, the normal grip determination unit 462 of the processor 460 may receive a signal (e.g., waveform) a obtained through the first light emitter (e.g., the IR LED 412) and the light receiver 415 and a signal (e.g., waveform) b obtained through the second light emitter (e.g., the red LED 414) and the light receiver 415. According to an exemplary embodiment, the normal grip determination unit 462 of the processor 460 may determine at least one of a correlation level at predetermined segments of the signal a obtained through the first light emitter (e.g., the IR LED 412) and the at least one light receiver 415, a correlation level at predetermined segments of the signal b obtained through the second light emitter (e.g., the red LED 414) and the at least one light receiver 415, and a correlation level between the signal a at a predetermined segment obtained through the first light emitter (e.g., the IR LED 412) and the at least one light receiver 415 and the signal b at a predetermined segment obtained through the second light emitter (e.g., the red LED 414) and the at least one light receiver to determine whether a first designated condition (e.g., a correlation level 1%-50%) or a second designated condition (e.g., a correlation level 50%-100%) is satisfied. According to an exemplary embodiment, the normal grip determination unit 462 may divide the received signals a and b into the same segment. For example, the normal grip determination unit 462 may divide the signals a and b received from the bio sensor 410 into two segments (e.g., segments 1 and 3 and segments 2 and 4 of FIG. 8). The normal grip determination unit 462 may determine a correlation level (e.g., 1 and 2) at each segment of the signal a, a correlation level (e.g., 3 and 4) at each segment of the signal b, a correlation level (e.g., (1) and (3), (2) and (4)) on each segment basis of the signals a and b, a correlation level (e.g., (1) and (2)) at each segment of the signal a, and a correlation level (e.g., 3 and 4) at each segment of the signal b. That is, when light is emitted through the first light emitter (e.g., the IR LED 412) and the second light emitter (e.g., the red LED 414) and when light reflected and returned through the external object (e.g., finger) of the user of the electronic device 400 is received through the light receiver 415, the normal grip determination unit 462 may check a waveform of the received light to determine a difference (or a correlation level) between the signals a and b (e.g., waveform) and to determine whether the signals satisfy a first designated condition or a second designated condition. For example, the normal grip determination unit 462 may determine whether a user finger accurately grips the bio sensor 410 based on any one signal of the signal a, the signal b, and the signals a and b.

According to an exemplary embodiment, as a portion of the second designated condition, if a user finger of the electronic device 400 accurately grips the bio sensor 410, the processor 460 may obtain biometric information (e.g., heart rate, oxygen saturation, stress) about the user of the electronic device 400 based on information received from the bio sensor 410 using the biometric information obtaining unit 464. According to an exemplary embodiment, as a correlation level determination result of the signals a and b, if a correlation level satisfies a second designated condition (e.g., 50%-100%), the processor 460 may store the signals a and b as a reference bio signal of the user of the electronic device 400 at the memory 450.

According to an exemplary embodiment, as a portion of the first designated condition, if a user finger of the electronic device 400 does not accurately grip the bio sensor 410, the processor 460 may determine whether the user finger is located at which side (e.g., the right or the left) based on a location of the bio sensor 410 using the normal grip determination unit 462. According to an exemplary embodiment, when the first light emitter (e.g., the IR LED 412) and the second light emitter (e.g., the red LED 414) are disposed at an upper portion and a lower portion of the light receiver 415, the processor 460 may determine whether the user finger is located at an upper portion or a lower portion based on a location of the bio sensor 410 using the normal grip determination unit 462. According to an exemplary embodiment, when the first light emitter (e.g., the IR LED 412), the second light emitter (e.g., the red LED 414), a third light emitter (e.g., green LED), and a fourth light emitter (e.g., blue LED) are disposed at an upper portion, lower portion, left side portion, and right side portion, respectively, of the light receiver 415 based on the light receiver 415, the processor 460 may determine whether the user finger is located at which side of an upper portion, lower portion, left side portion, and right side portion based on a location of the bio sensor 410 using the normal grip determination unit 462. In this case, the processor 460 may output an UI (e.g., graphic object) or a guide voice that guides a grip location of the user finger to accurately locate at the bio sensor 410 through the display 434 or the audio output unit 440.

Figure 9:
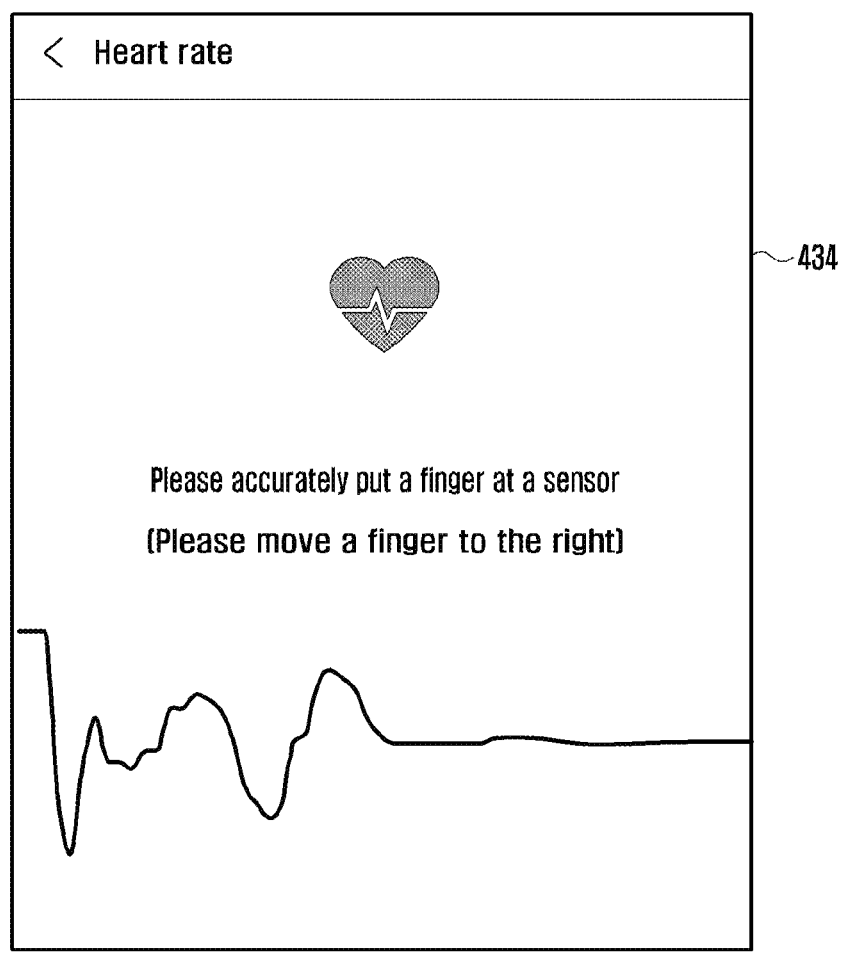
FIG. 9 is a diagram illustrating an example of a user interface (UI) that guides an accurate grip location of a user finger to a bio sensor through a display of an electronic device according to various exemplary embodiments of the present disclosure.

FIG. 9 is a diagram illustrating an example of an UI that guides an accurate grip location of a user finger to a bio sensor (e.g., the bio sensor 410 of FIG. 4) through a display (e.g., the display 434 of FIG. 4) of an electronic device according to various exemplary embodiments of the present disclosure.

With reference to FIG. 9, when the user finger of the electronic device 400 is not accurately located at the bio sensor 410 (e.g., when a grip location of the user finger of the electronic device 400 is located at the left of the bio sensor 410), the processor 460 may control the display 434 to display (e.g., please move a finger to the right.) an UI (e.g., graphic object) and to guide the user finger to accurately locate at the bio sensor 410.

Figure 10:
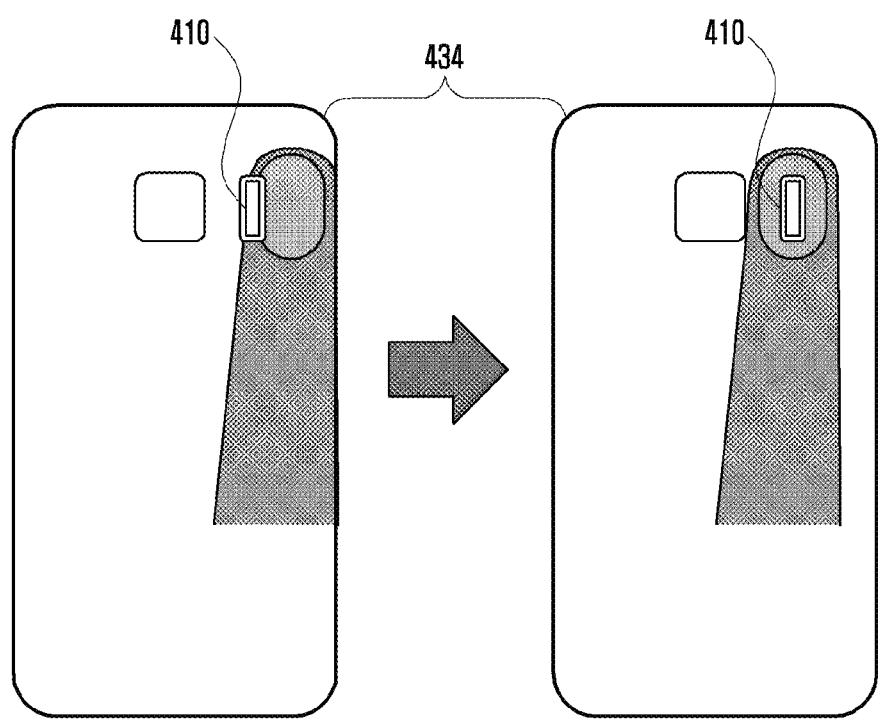
FIG. 10 is a diagram illustrating another example of an UI that guides an accurate grip location of a user finger to a bio sensor through a display of an electronic device according to various exemplary embodiments of the present disclosure.

FIG. 10 is a diagram illustrating another example of an UI that guides an accurate grip location of a user finger to a bio sensor (e.g., the bio sensor 410 of FIG. 4) through a display (e.g., the display 434 of FIG. 4) of an electronic device according to various exemplary embodiments of the present disclosure.

With reference to FIG. 10, when the user finger of the electronic device 400 is located in a right direction instead of being accurately located at the bio sensor 410, the processor 460 may control the display 434 to display an UI (e.g., graphic object) that guides a finger location to move to the left. According to an exemplary embodiment, when the user finger of the electronic device 400 is not accurately located at the bio sensor 410, the processor 460 may output (e.g., please move the finger to the left) a guide voice that guides to move a location of the user finger to accurately locate the user finger at the bio sensor 410 through the audio output unit 440.

Figure 11:
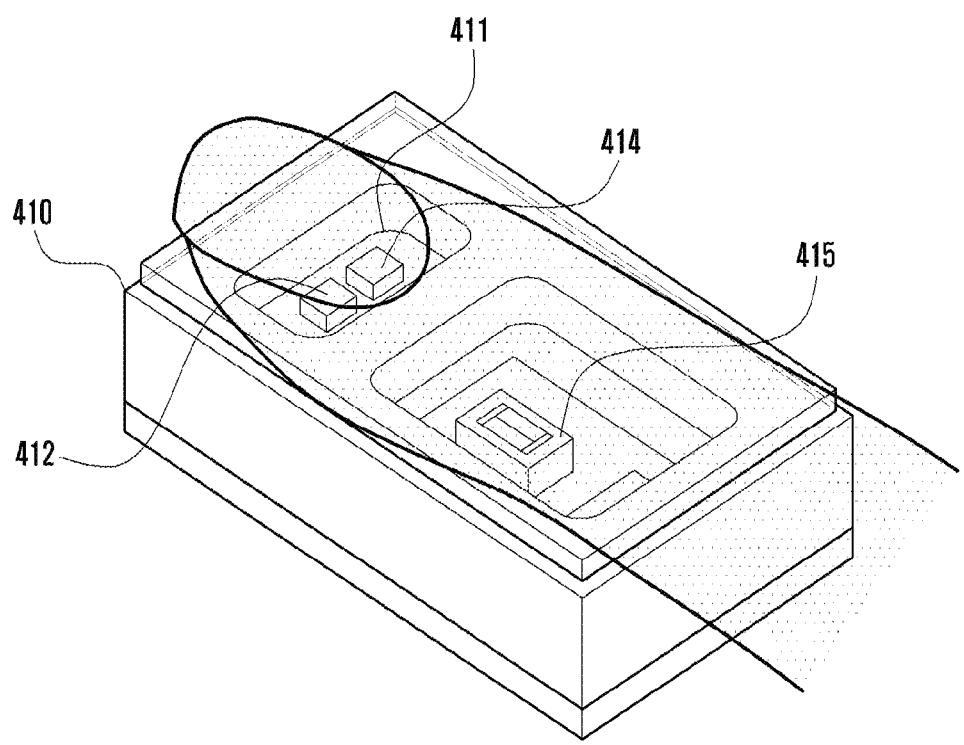
FIG. 11 is a diagram illustrating an example in which a user finger normally grips a bio sensor of an electronic device according to various exemplary embodiments of the present disclosure.
Figure 12A:
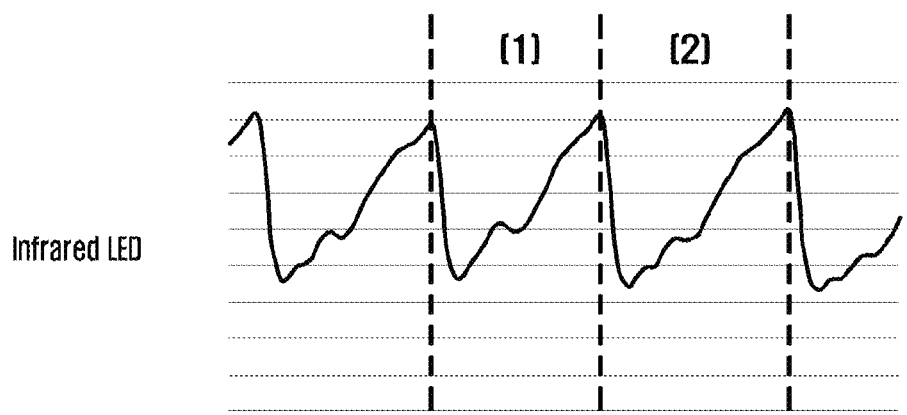
FIGS. 12A-12B are diagrams illustrating an example of determining a correlation level when a user finger normally grips a bio sensor of an electronic device according to various exemplary embodiments of the present disclosure.
Figure 12B:
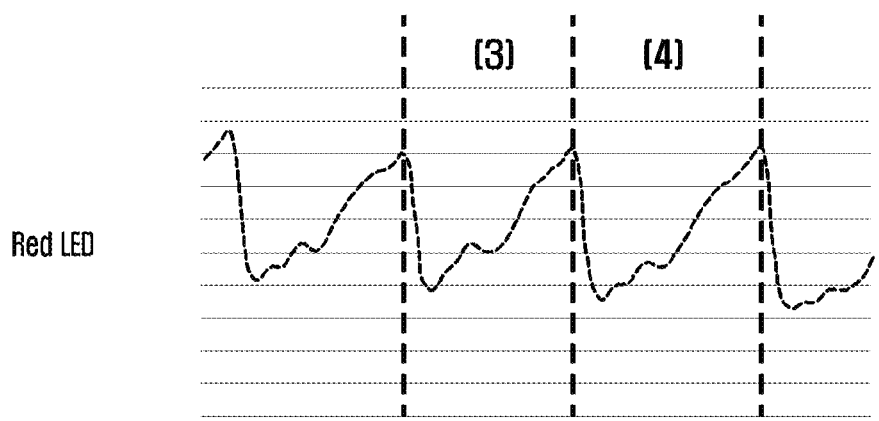

FIG. 11 is a diagram illustrating an example in which a user finger normally grips a bio sensor (e.g., the bio sensor 410 of FIG. 4) of an electronic device according to various exemplary embodiments of the present disclosure. FIGS. 12A and 12B are diagrams illustrating an example of determining a correlation level when a user finger normally grips a bio sensor of an electronic device according to various exemplary embodiments of the present disclosure.

With reference to FIG. 11, when the user finger is normally accurately located at the bio sensor 410, the light emitter 411 of the bio sensor 410 may emit light toward the user finger through the first light emitter (e.g., the IR LED 412) and the second light emitter (e.g., the red LED 414). The light receiver 415 of the bio sensor 410 may receive light reflected and returned through the user finger. The processor 460 may divide a signal (e.g., waveform) of the first light emitter (e.g., the IR LED 412) and a signal (e.g., waveform) of the second light emitter (e.g., the red LED 414) received through the light receiver 415 into at least one segment to determine a correlation level.

With reference to FIGS. 12A-12B, FIG. 12A illustrates a signal (e.g., waveform) obtained through the first light emitter (e.g., the IR LED 412) of the light emitter 411 and the light receiver 415, and FIG. 12B illustrates a signal (e.g., waveform) obtained through the second light emitter (e.g., the red LED 414) of the light emitter 411 and the light receiver 415.

With reference to signals (e.g., waveform) of FIGS. 12A and 12B, it may be determined that a correlation level (e.g., similarity level) at segments 1 and 2 of a signal a is high and that a correlation level at segments 3 and 4 of a signal b is high and that a correlation level at segments 1 and 2 of a signal a and segments 3 and 4 of a signal b is high. In this case, the processor 460 may determine that a user finger of the electronic device 400 accurately grips the bio sensor 410 through the normal grip determination unit 462. Further, the processor 460 may obtain biometric information (e.g., heart rate, oxygen saturation, stress) about the user of the electronic device 400 based on information received from the bio sensor 410 using the biometric information obtaining unit 464. According to an exemplary embodiment, a method of comparing the signals may be performed with various methods such as a magnitude, period, area, or pattern of the signal in addition to a correlation level. Waveform comparison algorithm may be implemented with various methods of comparing signals and is not limited to the foregoing method.

Figure 13:
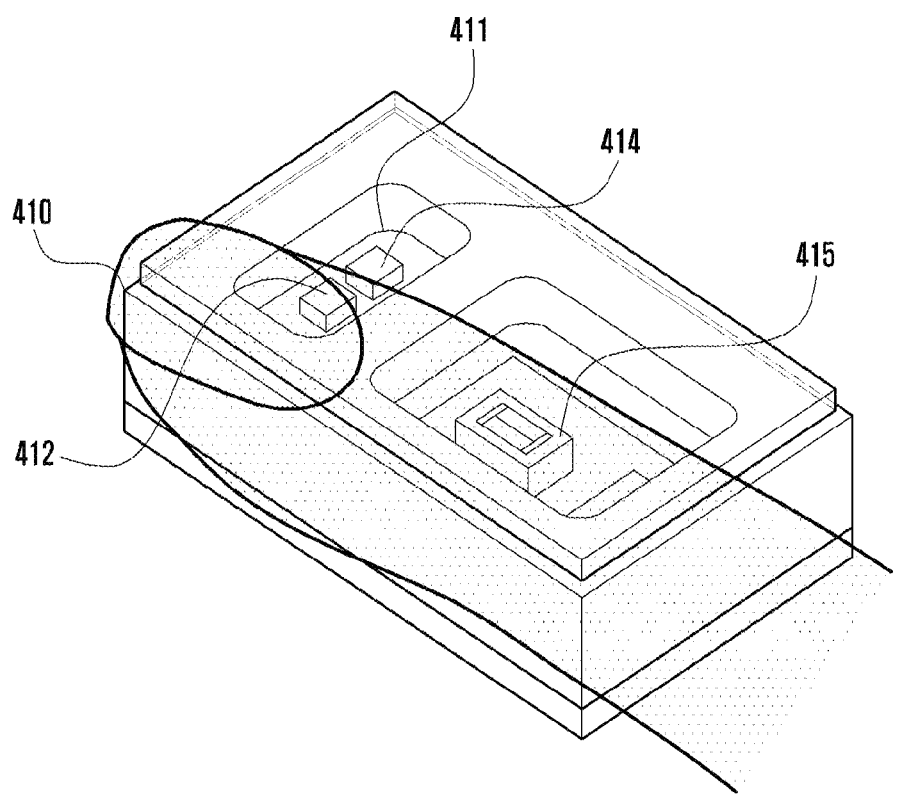
FIG. 13 is a diagram illustrating an example in which a user finger grips a bio sensor of an electronic device in a left direction according to various exemplary embodiments of the present disclosure.
Figure 14A:
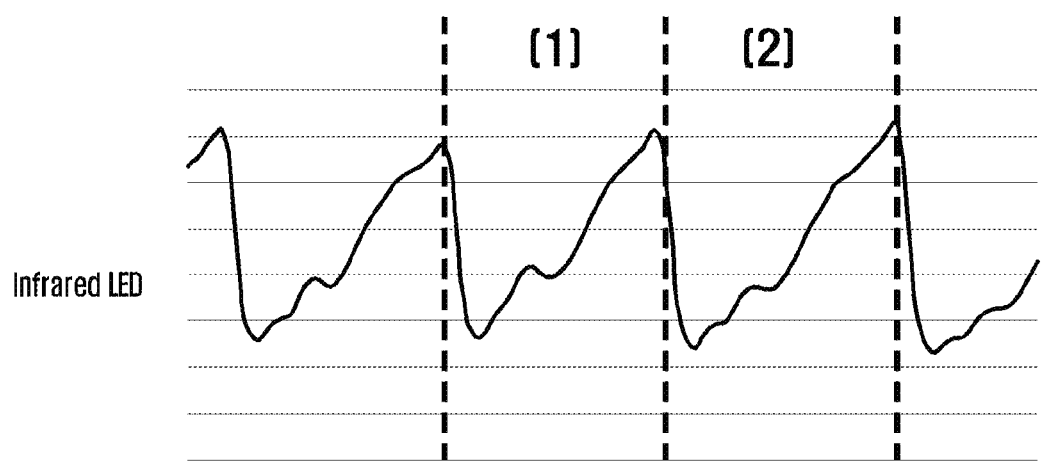
FIGS. 14A-14B are diagrams illustrating an example of determining a correlation level when a user finger grips a bio sensor of an electronic device in a left direction according to various exemplary embodiments of the present disclosure.
Figure 14B:
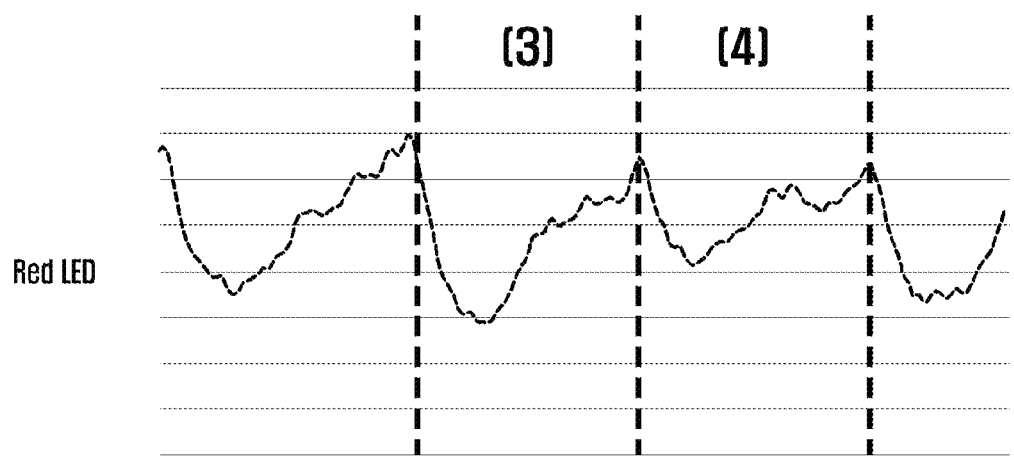

FIG. 13 is a diagram illustrating an example in which a user finger grips a bio sensor (e.g., the bio sensor 410 of FIG. 4) of an electronic device in a left direction according to various exemplary embodiments of the present disclosure. FIGS. 14A and 14B are diagrams illustrating an example of determining a correlation level when a user finger grips a bio sensor of an electronic device in a left direction according to various exemplary embodiments of the present disclosure.

With reference to FIG. 13, when the user finger grips the bio sensor 410 in a left direction instead of being accurately located at the bio sensor 410, the second light emitter (e.g., the red LED 414) of the light emitter 411 may be exposed to the outside. The processor 460 may receive more light by the first light emitter (e.g., the IR LED 412) and the user finger than light by the second light emitter (e.g., the red LED 414) and the user finger through the light receiver 415.

With reference to FIG. 14A-14B, FIG. 14A illustrates a signal (e.g., waveform) obtained through the first light emitter (e.g., the IR LED 412) of the light emitter 411 and the light receiver 415, and FIG. 14B illustrates a signal (e.g., waveform) obtained through the second light emitter (e.g., the red LED 414) of the light emitter 411 and the light receiver 415. In this case, because the second light emitter (e.g., the red LED 414) of the light emitter 411 is in an exposed state, a signal b of the second light emitter (e.g., the red LED 414) may be more irregular than a signal a of the first light emitter (e.g., the IR LED 412).

With reference to signals (e.g., waveform) of FIGS. 14A and 14B, it may be determined that a correlation level at segments 1 and 2 of the signal a is high and that a correlation level at segments 3 and 4 of the signal b is low and that a correlation level at segments 1 and 2 of the signal a and at segments 3 and 4 of the signal b is low. In this case, the processor 460 may compare a peak value of the signal a and a peak value of the signal b through the normal grip determination unit 462 to determine that the user finger of the electronic device 400 grips the bio sensor 410 in a left direction instead of accurately gripping the bio sensor 410. For example, as shown in FIG. 9, the processor 460 may output an UI (e.g., graphic object) or a guide voice that guides the user finger to move to the right through the display 434 or the audio output unit 440.

According to an exemplary embodiment, the processor 460 may determine using a value (e.g., Z-axis information) measured by an acceleration sensor (e.g., the acceleration sensor 240E of FIG. 2) whether the user views a front surface or a rear surface of the electronic device 400. According to an exemplary embodiment, when the user views a rear surface (e.g., the bio sensor 410) of the electronic device 400, the processor 460 may guide to move the user finger to the right. According to another exemplary embodiment, when the user views a front surface (e.g., the display 434) of the electronic device 400, the processor 460 may guide to move the user finger to the left.

According to an exemplary embodiment, as a determination result of a correlation level between the signals a and b, in a state in which the user finger of the electronic device 400 accurately grips the bio sensor 410, when the user finger moves to the left or the right, the processor 460 may determine that a correlation level of a finger grip location to the bio sensor 410 is lowered. In this case, the processor 460 may compare amplitudes of a reference bio signal of the user of the electronic device 400 stored at the memory 450 and a signal corresponding to a first designated condition in which a correlation level is lowered. The processor 460 may guide a relative distance in which a grip location of the user finger of the electronic device 400 is separated from the bio sensor 410. For example, if a correlation level between a reference bio signal of the user of the electronic device 400 stored at the memory 450 and a signal corresponding to the first designated condition is 50%-99%, the processor 460 may guide that the user finger has been a little moved to the left (or the right). For example, if a correlation level between a reference bio signal of the user of the electronic device 400 stored at the memory 450 and a signal corresponding to the first designated condition is 1%-49%, the processor 460 may guide that the user finger has been much moved to the left (or the right). In this case, the processor 460 may output a guide voice that guides the user finger to move to the right or the left through the audio output unit 440.

Figure 15:
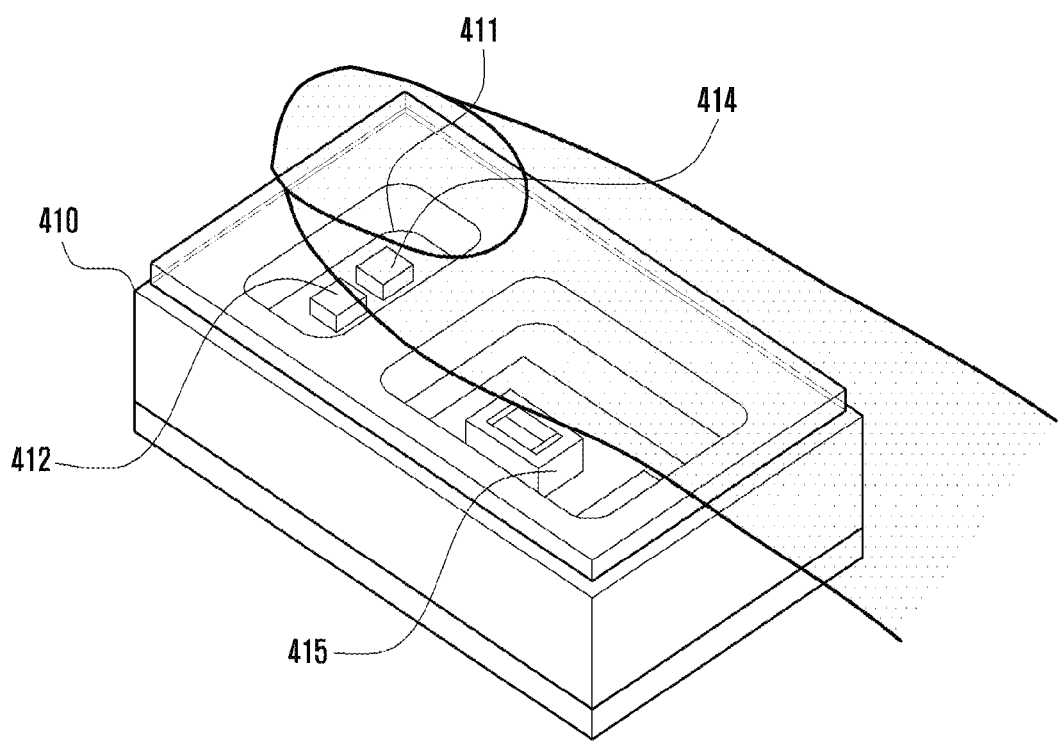
FIG. 15 is a diagram illustrating an example in which a user finger grips a bio sensor of an electronic device in a right direction according to various exemplary embodiments of the present disclosure.
Figure 16A:
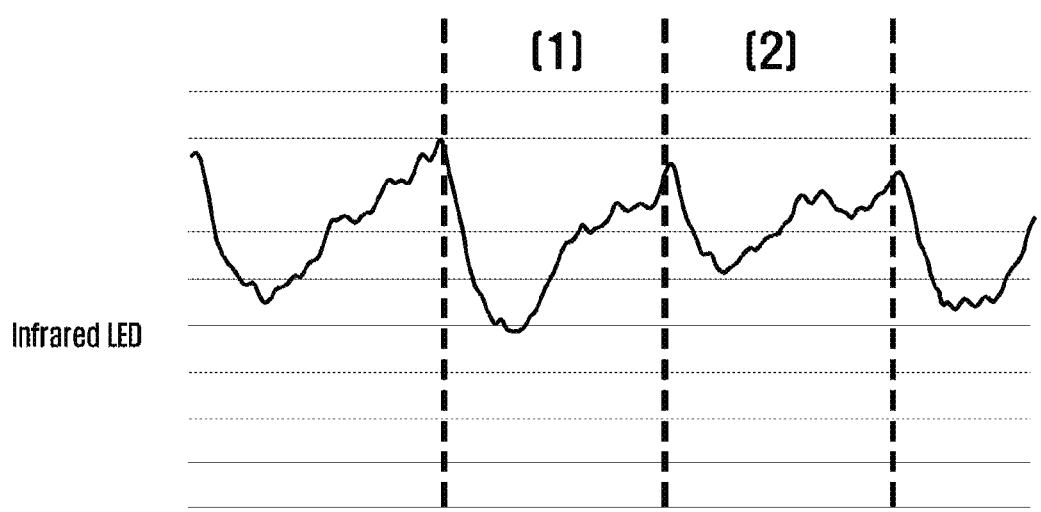
FIGS. 16A-16B are diagrams illustrating an example of determining a correlation level when a user finger grips a bio sensor of an electronic device in a right direction according to various exemplary embodiments of the present disclosure.
Figure 16B:
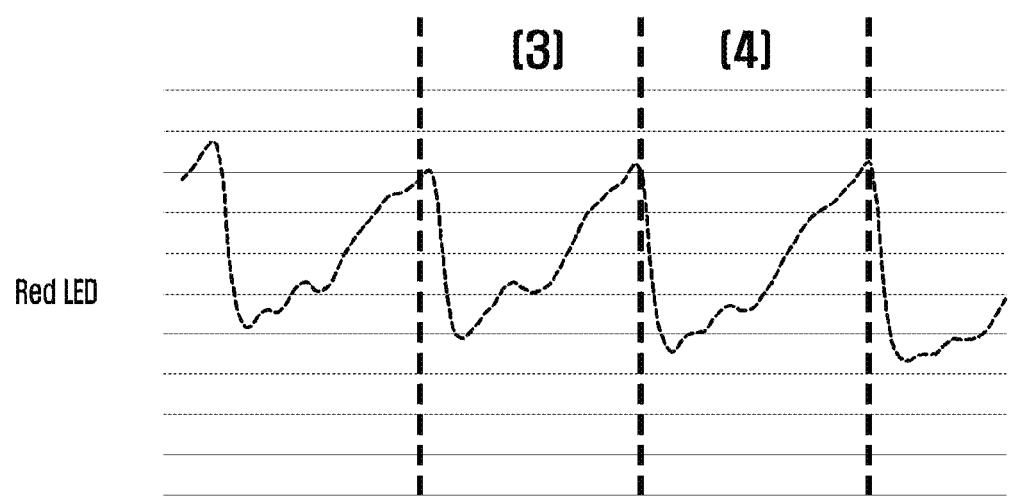

FIG. 15 is a diagram illustrating an example when a user finger grips in a right direction a bio sensor (e.g., the bio sensor 410 of FIG. 4) of an electronic device according to various exemplary embodiments of the present disclosure. FIGS. 16A and 16B are diagrams illustrating an example of determining a correlation level when a user finger grips in a right direction a bio sensor of an electronic device according to various exemplary embodiments of the present disclosure.

With reference to FIG. 15, when the user finger grips the bio sensor 410 in a right direction instead of accurately gripping the bio sensor 410, the first light emitter (e.g., the IR LED 412) of the light emitter 411 may be exposed to the outside. The processor 460 may receive more light by the second light emitter (e.g., the red LED 414) and the user finger than light by the first light emitter (e.g., the IR LED 412) and the user finger through the light receiver 415.

With reference to FIG. 16A-16B, FIG. 16A illustrates a signal (e.g., waveform) obtained through the first light emitter (e.g., the IR LED 412) of the light emitter 411 and the light receiver 415, and FIG. 16B illustrates a signal (e.g., waveform) obtained through the second light emitter (e.g., the red LED 414) of the light emitter 411 and the light receiver 415. In this case, because the first light emitter (e.g., the IR LED 412) of the light emitter 411 is in an exposed state, a signal a of the first light emitter (e.g., the IR LED 412) may be more irregular than a signal b of the second light emitter (e.g., the red LED 414).

With reference to signals (e.g., waveforms) of FIGS. 16A and 16B, it may be determined that a correlation level at segments 1 and 2 of the signal a is low and that a correlation level at segments 3 and 4 of the signal b is high and that a correlation level at segments 1 and 2 of the signal a and at segments 3 and 4 of the signal b is low. In this case, the processor 460 may compare a peak value of the signal a and a peak value of the signal b through the normal grip determination unit 462 to determine that the user finger of the electronic device 400 grips in a right direction instead of accurately gripping the bio sensor 410. For example, as shown in FIG. 10, the processor 460 may output an UI (e.g., graphic object) or a guide voice that guides the user finger to move to the left through the display 434 or the audio output unit 440.

According to an exemplary embodiment, the processor 460 may determine using a value (e.g., Z-axis information)

measured by an acceleration sensor (e.g., the acceleration sensor 240E of FIG. 2) whether the user views a front surface or a rear surface of the electronic device 400. According to an exemplary embodiment, the processor 460 may guide the user finger to move to the left when the user views a rear surface (e.g., the bio sensor 410) of the electronic device 400. According to another exemplary embodiment, when the user views a front surface (e.g., the display 434) of the electronic device 400, the processor 460 may guide the user finger to move to the right.

According to an exemplary embodiment, if a correlation level between a signal (e.g., waveform) a obtained through the first light emitter (e.g., the IR LED 412) of the light emitter 411 and the light receiver 415 and a signal (e.g., waveform) b obtained through the second light emitter (e.g., the red LED 414) of the light emitter 411 and the light receiver 415 is a threshold or less (e.g., 1%-50%), the processor 460 may determine whether biometric information about the user of the electronic device 400 can be obtained using any one of the first light emitter (e.g., the IR LED 412) and the second light emitter (e.g., the red LED 414). For example, the processor 460 may determine a correlation level between the signal (e.g., waveform) a obtained through the first light emitter (e.g., the IR LED 412) of the light emitter 411 and the light receiver 415 and the signal (e.g., waveform) b obtained through the second light emitter (the red LED 414) of the light emitter 411 and the light receiver 415 and determine whether the user finger of the electronic device 400 is located at which side (e.g., the first light emitter (e.g., the IR LED 412) or the second light emitter (e.g., the upper end of the red LED 414)) of the bio sensor 410. In this case, the processor 460 may obtain the user's biometric information using any one of the first light emitter (e.g., the IR LED 412) and the second light emitter (e.g., the red LED 414) corresponding to a grip location of the user finger of the electronic device 400.

According to an exemplary embodiment, if a correlation level between the signal (e.g., waveform) a obtained through the first light emitter (e.g., the IR LED 412) of the light emitter 411 and the light receiver 415 and the signal (e.g., waveform) b obtained through the second light emitter (e.g., the red LED 414) of the light emitter 411 and the light receiver 415 is a threshold or less (e.g., 1%-50%) and if the user's biometric information cannot be obtained using any one of the second light emitter (e.g., the red LED 414) and the first light emitter (e.g., the IR LED 412), the processor 460 may output an UI (e.g., graphic object) or a guide voice that guides to move the user finger to the left or the right through the display 434 or the audio output unit 440.

Figure 17:
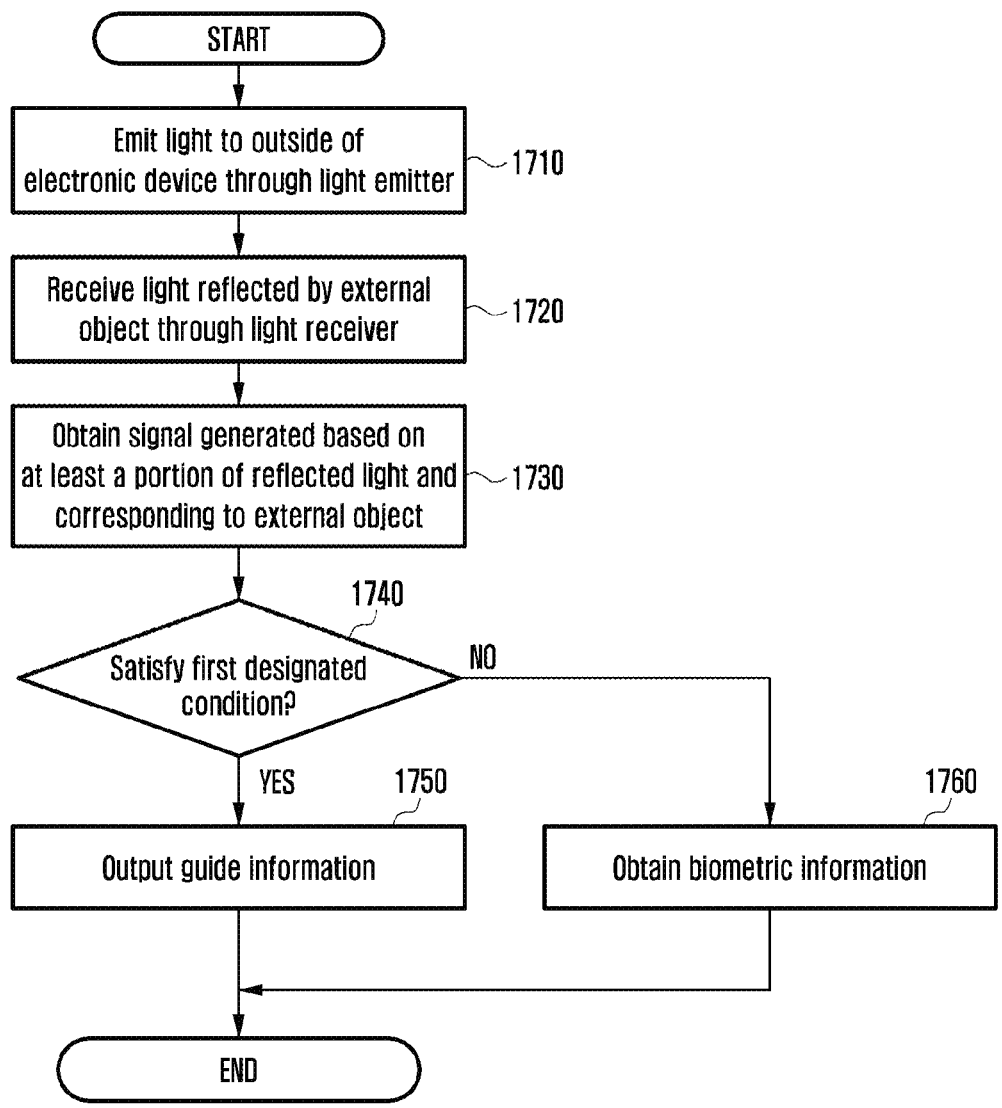
FIG. 17 is a flowchart illustrating a method of an example in which an electronic device measures a user's biometric information according to various exemplary embodiments of the present disclosure.

FIG. 17 is a flowchart illustrating a method of an example in which an electronic device measures the user's biometric information according to various exemplary embodiments of the present disclosure.

The processor 460 may emit light to the outside of the electronic device 400 through at least one light emitter 411 (e.g., infrared light emitting circuit) at operation 1710.

The processor 460 may receive (obtain) light reflected by the external object (e.g., finger) among light emitted from the light emitter 411 through the light receiver 415 (e.g., infrared light detection circuit) at operation 1720.

The processor 460 may obtain a signal generated based on at least a portion of the light reflected by the external object (e.g., finger) and corresponding to the external object (e.g., finger) at operation 1730.

The processor 460 may determine whether a reference bio signal of the user of the electronic device 400 stored at the memory 450 and the signal obtained at operation 1730 satisfy a first designated condition (e.g., a correlation level 1-50%) at operation 1740.

If a reference bio signal of the user of the electronic device 400 stored at the memory 450 and the signal obtained at operation 1730 satisfy a first designated condition (e.g., a correlation level 1%-50%), the processor 460 may output guide information (e.g., UI or guide voice) related to a location of the external object (e.g., finger) to the light emitter 411 and the light receiver 415 through the display 434 or the audio output unit 440 at operation 1750.

If a reference bio signal of the user of the electronic device 400 stored at the memory 450 and the signal obtained at operation 1730 satisfy a second designated condition (e.g., a correlation level 50%-100%) instead of satisfying the first designated condition (e.g., a correlation level 1%-50%), the processor 460 may obtain biometric information about the external object (e.g., finger) at operation 1760.

Figure 18:
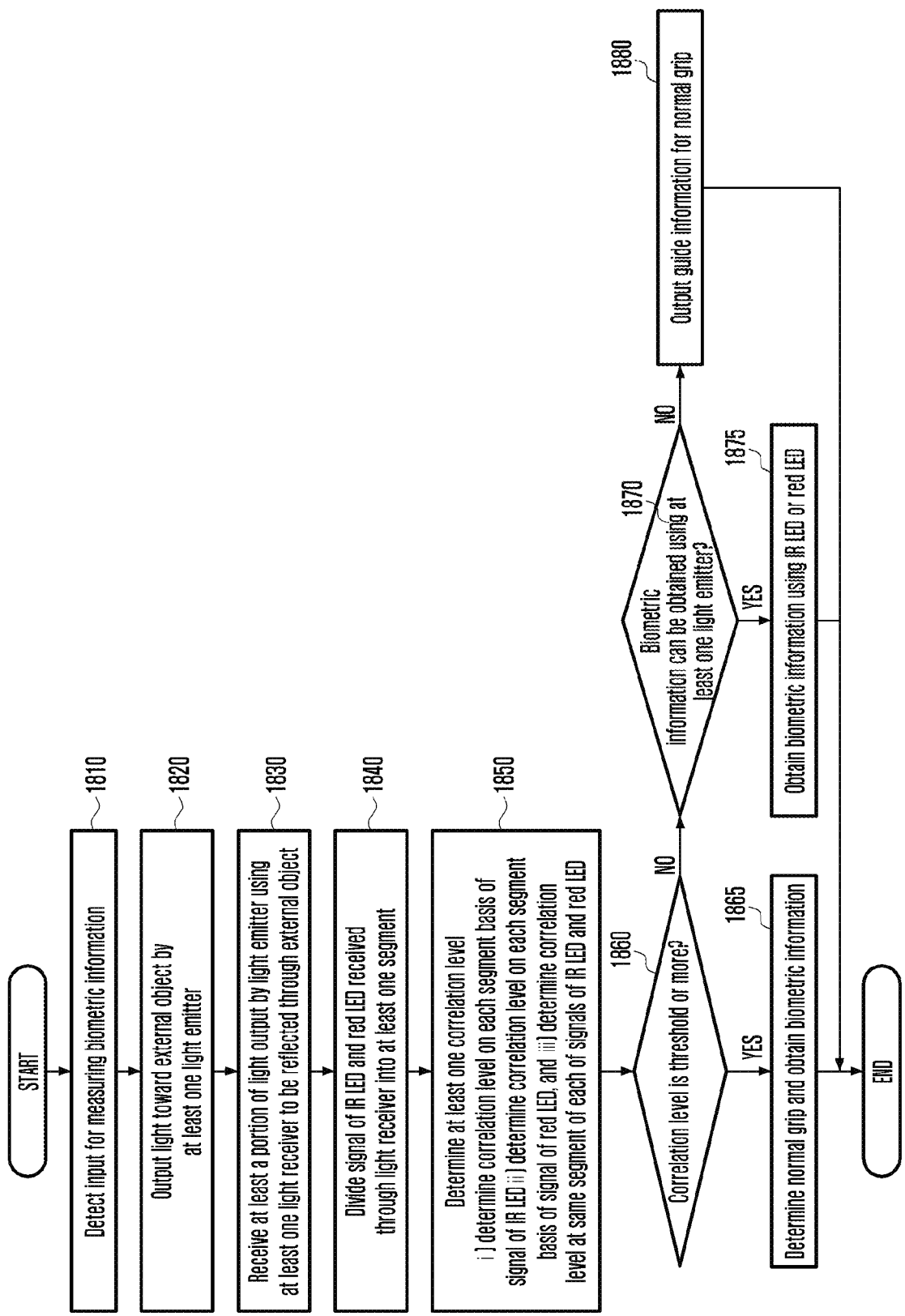
FIG. 18 is a flowchart illustrating a method of another example in which an electronic device measures a user's biometric information according to various exemplary embodiments of the present disclosure.

FIG. 18 is a flowchart illustrating a method of another example in which an electronic device measures the user's biometric information according to various exemplary embodiments of the present disclosure.

The processor 460 may detect at least one input for measuring biometric information about the user of the electronic device 400 through the bio sensor 410 at operation 1810.

For example, in order to measure biometric information, the processor 460 may receive at least one of a touch input, voice input, and gesture input using the user finger of the electronic device 400. When a predetermined period (e.g., 1 day-5 days) has come in order to measure biometric information, the processor 460 may determine this to one input.

The processor 460 may output light toward the external object (e.g., finger) of the electronic device 400 by at least one light emitter 411 (e.g., infrared light emitting circuit) provided at the bio sensor 410 at operation 1820. For example, the processor 460 may output light to the external object (e.g., finger) through the second light emitter (e.g., the red LED 414) and the first light emitter (e.g., the IR LED 412) of the light emitter 411.

The processor 460 may receive at least a portion of light emitted by the light emitter 411 to be reflected through the external object (e.g., finger) using at least one light receiver 415 (e.g., infrared light detection circuit) at operation 1830.

The processor 460 may divide a signal of the first light emitter (e.g., the IR LED 412) and the second light emitter (e.g., the red LED 414) of the light emitter 411 received through the light receiver 415 into at least one segment at operation 1840.

The processor 460 may determine at least one correlation level of i) a correlation level on each segment basis of a signal of the first light emitter (e.g., the IR LED 412), ii) a correlation level on each segment basis of a signal of the second light emitter (e.g., the red LED 414), and iii) a correlation level at the same segment of each of a signal of the first light emitter (e.g., the IR LED 412) and a signal of the second light emitter (e.g., the red LED 414) at operation 1850.

The processor 460 may determine whether a correlation level at the same segment of each of a signal of the first light emitter (e.g., the IR LED 412) and a signal of the second light emitter (e.g., the red LED 414) is a threshold or more (e.g., a correlation level 50%-100%) at operation 1860.

If a correlation level at the same segment of each of a signal of the first light emitter (e.g., the IR LED 412) and a signal of the second light emitter (e.g., the red LED 414) is a threshold or more (e.g., a correlation level 50%-100%), the processor 460 may determine that the user finger of the electronic device 400 normally grips the bio sensor 410 to obtain the user's biometric information at operation 1865.

If a correlation level is less than a threshold, the processor 460 may determine whether biometric information about the user of the electronic device 400 can be obtained using at least one light emitter 411 (e.g., the first light emitter (e.g., the IR LED 412) or the second light emitter (e.g., the red LED 414)) at operation 1870.

If biometric information about the user of the electronic device 400 can be obtained using at least one light emitter 411 (e.g., the first light emitter (e.g., the IR LED 412) or the second light emitter (e.g., the red LED 414) (e.g., IR LED 412 or the red LED 414)), the processor 460 may obtain biometric information about the user of the electronic device 400 using the first light emitter (e.g., the IR LED 412) or the second light emitter (e.g., the red LED 414) at operation 1875.

If biometric information about the user of the electronic device 400 cannot be obtained using at least one light emitter 411 (e.g., the first light emitter (e.g., the IR LED 412) or the second light emitter (e.g., the red LED 414) (e.g., IR LED 412 or the red LED 414)), the processor 460 may output guide information (e.g., UI or guide voice) related to an accurate grip location of the external object (e.g., finger) to the light emitter 411 and the light receiver 415 through the display 434 or the audio output unit 440 at operation 1880.

Figure 19:
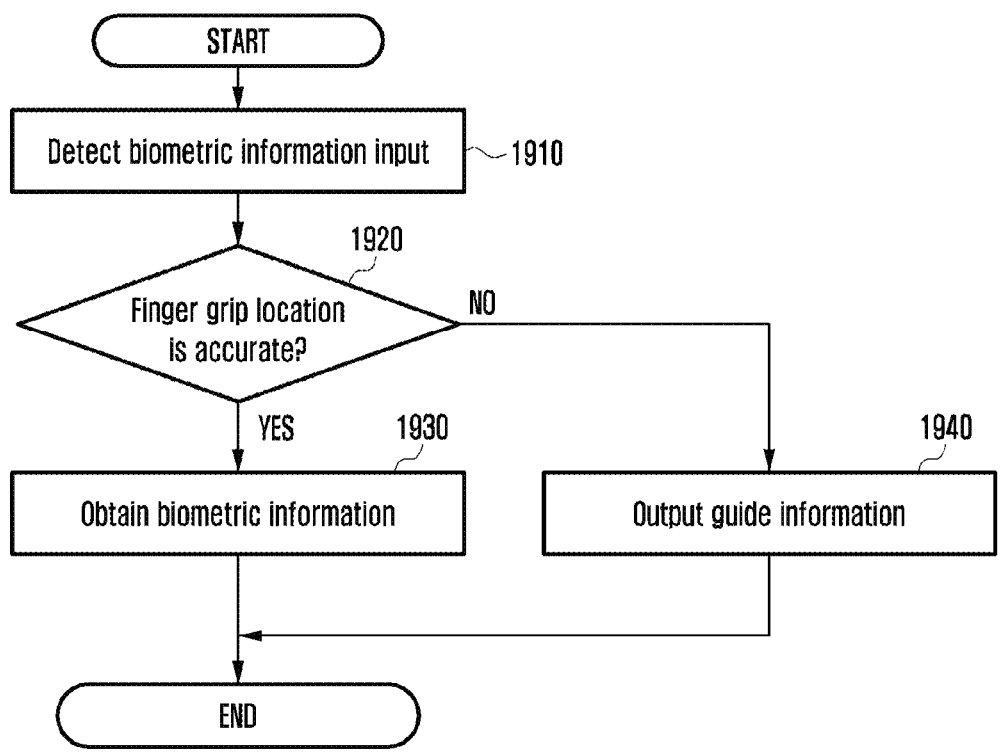
FIG. 19 is a flowchart illustrating a method of another example in which an electronic device measures a user's biometric information according to various exemplary embodiments of the present disclosure.

FIG. 19 is a flowchart illustrating a method of another example in which an electronic device measures the user's biometric information according to various exemplary embodiments of the present disclosure.

The processor 460 may detect at least one input for measuring biometric information of the user of the electronic device 400 through the bio sensor 410 at operation 1910.

The processor 460 may determine through the normal grip determination unit 462 whether a user finger grip location to the bio sensor 410 is accurate at operation 1920. According to an exemplary embodiment, as shown in FIG. 6C, the processor 460 of the electronic device 400 may detect a grip location of the user finger of the electronic device 400 to the bio sensor 410 through the light receiver 415 configured in a form in which a first photodiode PD1 to a fourth photodiode PD4 are disposed at an upper portion, left side portion, lower portion, and right side portion, respectively, based on a central hole. According to another exemplary embodiment, as shown in FIG. 7, the processor 460 of the electronic device 400 may detect a grip location of the user finger of the electronic device 400 to the bio sensor 410 through the digitizer 420 configured with the first driver 422 and the second driver 424.

If a user finger grip location to the bio sensor 410 is accurate, the processor 460 may obtain the user's biometric information at operation 1930.

If a user finger grip location to the bio sensor 410 is not accurate, the processor 460 may output guide information (e.g., UI or guide voice) that guides to move the user finger of the electronic device 400 through the display 434 or the audio output unit 440 at operation 1940.

Therefore, the electronic device 400 according to various exemplary embodiments of the present disclosure can determine whether the user finger normally grips the bio sensor 410 to measure accurate biometric information about the user of the electronic device 400. Further, if a user finger grip location to the bio sensor 410 is not accurate, the electronic device 400 may provide guide information for normal grip to the user.

According to various exemplary embodiments of the present disclosure, by guiding an accurate grip location of a bio sensor provided in an electronic device to a user, biometric information about the user of the electronic device can be accurately measured.

Although exemplary embodiments of the present disclosure have been described in detail hereinabove it should be clearly understood that many variations and modifications of the basic inventive concepts herein described that may appear to those skilled in the art will still fall within the spirit and scope of the exemplary embodiments of the present disclosure as defined in the appended claims.

What is claimed is:

1. An electronic device comprising:
   at least one light emitter;
   a light receiver;
   a digitizer formed at a periphery of the at least one light emitter and the light receiver, the digitizer being configured to detect location information comprising a touch coordinate; and
   a processor operably connected to the at least one light emitter and the light receiver, wherein the processor is configured to:
      emit light outside of the electronic device through the at least one light emitter,
      obtain, through the light receiver, light reflected by an external object among the emitted light,
      obtain a signal generated based on at least a portion of the reflected light and corresponding to the external object through the digitizer and receive the detected location information from the digitizer,
      output guide information related to a location of the external object when the signal satisfies a first designated condition, and
      obtain biometric information about the external object when the signal satisfies a second designated condition,
   wherein the light receiver comprises a plurality of photodiodes, and the light receiver is configured with at least one of a form in which the photodiodes are integrated, a form in which the photodiodes are disposed parallel to a predetermined direction, or a form in which the photodiodes are disposed at each of an upper portion, a left side portion, a lower portion, and a right side portion based on a central hole of the light receiver.

2. The electronic device of claim 1, further comprising a display,
   wherein the processor is configured to display a user interface (UI) for the guide information related to the location of the external object through the display when the first designated condition is satisfied.

3. The electronic device of claim 1, further comprising an audio output unit,
   wherein the processor is configured to output audio for the guide information related to the location of the external object through the audio output unit when the first designated condition is satisfied.

4. The electronic device of claim 1, wherein the at least one light emitter comprises a first light emitter and a second light emitter.

5. The electronic device of claim 4, wherein the processor is configured to obtain the biometric information about the external object using at least one of the first light emitter or the second light emitter when a correlation level between (i) a signal generated based on light emitted by the first light emitter and obtained through the light receiver and (ii) a signal generated based on light emitted by the second light emitter and obtained through the light receiver satisfies the first designated condition.

6. The electronic device of claim 4, wherein to determine whether the first designated condition or the second designated condition is satisfied, the processor is configured to determine at least one of:
- a correlation level at predetermined segments of a signal generated based on light emitted by the first light emitter and obtained through the light receiver,
- a correlation level at predetermined segments of a signal generated based on light emitted by the second light emitter and obtained through the light receiver, or
- a correlation level between (i) the signal generated based on light emitted by the first light emitter and obtained through the light receiver at a predetermined segment and (ii) the signal generated based on light emitted by the second light emitter and obtained through the light receiver at a predetermined segment.

7. The electronic device of claim 6, wherein the processor is configured to obtain the biometric information about the external object using at least one of the first light emitter or the second light emitter when the at least one of the correlation levels satisfies a third designated condition.

8. The electronic device of claim 1, further comprising a memory configured to store a reference bio signal of the external object measured through the light receiver,
wherein the processor is configured to determine whether the reference bio signal and the signal satisfy the first designated condition or the second designated condition.

9. A method of measuring biometric information using an electronic device, the method comprising:
- emitting light outside of the electronic device through at least one light emitter;
- obtaining, through a light receiver, light reflected by an external object among the emitted light;
- obtaining a signal generated based on at least a portion of the reflected light and corresponding to the external object through a digitizer formed at a periphery of the at least one light emitter and the light receiver, the digitizer being configured to detect location information comprising a touch coordinate;
- outputting, when the signal satisfies a first designated condition, guide information related to a location of the external object; and
- obtaining, when the signal satisfies a second designated condition, biometric information about the external object,
- wherein obtaining the light reflected by the external object comprises obtaining the light reflected by the external object among the emitted light using a plurality of photodiodes in the light receiver in at least one of a form in which the photodiodes included in the light receiver are integrated, a form in which the photodiodes are disposed parallel to a predetermined direction, or a form in which the photodiodes are disposed at each of an upper portion, a left side portion, a lower portion, and a right side portion based on a central hole of the light receiver.

10. The method of claim 9, wherein outputting the guide information related to the location of the external object comprises outputting a user interface (UI) through a display to guide movement of the location of the external object.

11. The method of claim 9, wherein outputting the guide information related to the location of the external object comprises outputting audio through an audio output unit to guide movement of the location of the external object.

12. The method of claim 9, wherein:
- the at least one light emitter comprises a first light emitter and a second light emitter, and
- emitting the light outside of the electronic device comprises emitting the light through at least one of the first light emitter or the second light emitter.

13. The method of claim 12, wherein obtaining the biometric information about the external object comprises obtaining the biometric information using at least one of the first light emitter or the second light emitter when a correlation level between (i) a signal generated based on light emitted by the first light emitter and obtained through the light receiver and (ii) a signal generated based on light emitted by the second light emitter and obtained through the light receiver satisfies the first designated condition.

14. The method of claim 12, further comprising determining whether the first designated condition or the second designated condition is satisfied by determining at least one of:
- a correlation level at predetermined segments of a signal generated based on light emitted by the first light emitter and obtained through the light receiver,
- a correlation level at predetermined segments of a signal generated based on light emitted by the second light emitter and obtained through the light receiver, or
- a correlation level between (i) the signal generated based on light emitted by the first light emitter and obtained through the light receiver at a predetermined segment and (ii) the signal generated based on light emitted by the second light emitter and obtained through the light receiver at a predetermined segment.

15. The method of claim 14, wherein obtaining the biometric information about the external object comprises obtaining the biometric information about the external object using at least one of the first light emitter or the second light emitter when the at least one of the correlation levels satisfies a third designated condition.

* * * * *